United States Patent
Jiao

(10) Patent No.: US 12,221,466 B2
(45) Date of Patent: Feb. 11, 2025

(54) TCR, POLYPEPTIDE, EXPRESSION VECTOR, HOST CELL, PHARMACEUTICAL COMPOSITION AND METHOD FOR OBTAINING TCR

(71) Applicants: Shiping Jiao, Jiangsu (CN); Keshihua (Nanjing) Biotechnology Co., Ltd, Jiangsu (CN)

(72) Inventor: Shiping Jiao, Jiangsu (CN)

(73) Assignees: Shiping Jiao, Nanjing (CN); Kshihua (Nanjing) Biotechnology Co., Ltd, Nanjing (CN)

(*) Notice: Subject to any disclaimer, the term of this patent is extended or adjusted under 35 U.S.C. 154(b) by 148 days.

(21) Appl. No.: 17/739,317

(22) Filed: May 9, 2022

(65) Prior Publication Data
US 2023/0028781 A1  Jan. 26, 2023

(30) Foreign Application Priority Data
Mar. 9, 2021 (CN) .............................. 202110258515

(51) Int. Cl.
C07K 14/705 (2006.01)
A61K 39/00 (2006.01)
A61P 35/00 (2006.01)
C07K 14/47 (2006.01)
C07K 14/725 (2006.01)

(52) U.S. Cl.
CPC ...... *C07K 14/7051* (2013.01); *A61K 39/4611* (2023.05); *A61K 39/4632* (2023.05); *A61K 39/464486* (2023.05); *A61P 35/00* (2018.01); *C07K 14/4748* (2013.01); *A61K 2239/31* (2023.05); *A61K 2239/38* (2023.05); *A61K 2239/55* (2023.05)

(58) Field of Classification Search
CPC .................................................. C07K 14/7051
USPC ...................................................... 424/139.1
See application file for complete search history.

(56) References Cited

PUBLICATIONS

Caivano et al (Journal of Immunological Methods, 2001, 255: 125-134).*

\* cited by examiner

*Primary Examiner* — Sean E Aeder
(74) *Attorney, Agent, or Firm* — JCIPRNET

(57) ABSTRACT

Disclosed in the present application is a T cell receptor (TCR) capable of specifically recognizes MAGE-A4 antigenic peptide, including a TCRα Polypeptide having at least 90% identity with any one selected from a group consisting of sequences of SEQ ID No: 1 to SEQ ID No: 30 and a TCRβ polypeptide having at least 90% identity with any one selected from a group consisting of sequences of SEQ ID No: 31 to SEQ ID No: 60, in which the TCRα polypeptides are in one-to-one correspondence with the TCRβ polypeptides in order.

17 Claims, 15 Drawing Sheets

Specification includes a Sequence Listing.

```
                       SEQUENCE LISTING

<160> NUMBER OF SEQ ID NOS: 255

<210> SEQ ID NO 1
  <211> LENGTH: 145
  <212> TYPE: PRT
  <213> ORGANISM: Artificial Sequence
  <220> FEATURE:
  <223> OTHER INFORMATION: Synthetic
  <220> FEATURE:
  <221> NAME/KEY: misc_feature
  <222> LOCATION: (145)..(145)
  <223> OTHER INFORMATION: Xaa can be any naturally occurring amino acid

<400> SEQUENCE: 1

Met Val Leu Lys Phe Ser Val Ser Ile Leu Trp Ile Gln Leu Ala Trp
  1               5                   10                  15

Val Ser Thr Gln Leu Leu Glu Gln Ser Pro Gln Phe Leu Ser Ile Gln
                  20                  25                  30

Glu Gly Glu Asn Leu Thr Val Tyr Cys Asn Ser Ser Ser Val Phe Ser
              35                  40                  45

Ser Leu Gln Trp Tyr Arg Gln Glu Pro Gly Gly Pro Val Leu Leu
          50                  55                  60

Val Thr Val Val Thr Gly Gly Glu Val Lys Lys Leu Lys Arg Leu Thr
  65                  70                  75                  80

Phe Gln Phe Gly Asp Ala Arg Lys Asp Ser Ser Leu His Ile Thr Ala
                  85                  90                  95

Ala Gln Pro Gly Asp Thr Gly Leu Tyr Leu Cys Ala Gly Asp Gly Ser
                  100                 105                 110

Gly Asn Thr Gly Lys Leu Ile Phe Gly Gln Gly Thr Thr Leu Gln Val
              115                 120                 125

Lys Pro Asp Ile Gln Asn Pro Asp Pro Ala Val Tyr Gln Leu Arg Asp
          130                 135                 140

Xaa
  145

<210> SEQ ID NO 2
  <211> LENGTH: 150
  <212> TYPE: PRT
  <213> ORGANISM: Artificial Sequence
  <220> FEATURE:
  <223> OTHER INFORMATION: Synthetic
  <220> FEATURE:
  <221> NAME/KEY: misc_feature
  <222> LOCATION: (150)..(150)
  <223> OTHER INFORMATION: Xaa can be any naturally occurring amino acid

<400> SEQUENCE: 2

Met Leu Leu Glu His Leu Leu Ile Ile Leu Trp Met Gln Leu Thr Trp
  1               5                   10                  15

Val Ser Gly Gln Gln Leu Asn Gln Ser Pro Gln Ser Met Phe Ile Gln
                  20                  25                  30

Glu Gly Glu Asp Val Ser Met Asn Cys Thr Ser Ser Ser Ile Phe Asn
```

```
                    35                  40                  45
Thr Trp Leu Trp Tyr Lys Gln Asp Pro Gly Glu Gly Pro Val Leu Leu
 50                  55                  60

Ile Ala Leu Tyr Lys Ala Gly Glu Leu Thr Ser Asn Gly Arg Leu Thr
 65                  70                  75                  80

Ala Gln Phe Gly Ile Thr Arg Lys Asp Ser Phe Leu Asn Ile Ser Ala
                 85                  90                  95

Ser Ile Pro Ser Asp Val Gly Ile Tyr Phe Cys Ala Gly Ala Gly Gly
                100                 105                 110

Phe Leu Asn Ser Gly Gly Ser Lys Tyr Lys Leu Thr Phe Gly Lys Gly
                115                 120                 125

Thr Leu Leu Thr Val Asn Pro Asn Ile Gln Asn Pro Asp Pro Ala Val
                130                 135                 140

Tyr Gln Leu Arg Asp Xaa
145                 150

<210> SEQ ID NO 3
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 3

Met Thr Arg Val Ser Leu Leu Trp Ala Val Val Val Ser Thr Cys Leu
 1               5                  10                  15

Glu Ser Gly Met Ala Gln Thr Val Thr Gln Ser Gln Pro Glu Met Ser
                 20                  25                  30

Val Gln Glu Ala Glu Thr Val Thr Leu Ser Cys Thr Tyr Asp Thr Ser
                 35                  40                  45

Glu Ser Asn Tyr Tyr Leu Phe Trp Tyr Lys Gln Pro Pro Ser Arg Gln
 50                  55                  60

Met Ile Leu Val Ile Arg Gln Glu Ala Tyr Lys Gln Gln Asn Ala Thr
 65                  70                  75                  80

Glu Asn Arg Phe Ser Val Asn Phe Gln Lys Ala Ala Lys Ser Phe Ser
                 85                  90                  95

Leu Lys Ile Ser Asp Ser Gln Leu Gly Asp Thr Ala Met Tyr Phe Cys
                100                 105                 110

Ala Phe Met Lys Gly Ser Asn Tyr Lys Leu Thr Phe Gly Lys Gly Thr
                115                 120                 125

Leu Leu Thr Val Asn Pro Asn Ile Gln Asn Pro Asp Pro Ala Val Tyr
                130                 135                 140

Gln Leu Arg Asp Xaa
145

<210> SEQ ID NO 4
<211> LENGTH: 135
<212> TYPE: PRT
<213> ORGANISM: Artificial Sequence
<220> FEATURE:
<223> OTHER INFORMATION: Synthetic

<400> SEQUENCE: 4

Met Thr Arg Val Ser Leu Leu Trp Ala Val Val Val Ser Thr Cys Leu
 1               5                  10                  15
```

```
Glu Ser Gly Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Asn Asn Tyr Tyr Leu Phe Trp Tyr Lys Gln Pro Pro Ser Arg Gln
 50                  55                  60

Met Ile Leu Val Ile Arg Gln Glu Ala Tyr Lys Gln Asn Ala Thr
 65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Thr His Ser Gly Ala Gly Ser Tyr Gln Leu Thr Phe Gly Lys Gly
            115                 120                 125

Thr Lys Leu Ser Val Ile Pro
            130                 135
```

<210> SEQ ID NO 5
<211> LENGTH: 144
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (144)..(144)
<223> OTHER INFORMATION: Xaa can be any naturally occurring amino acid

<400> SEQUENCE: 5

```
Met Leu Leu Ile Thr Ser Met Leu Val Leu Trp Met Gln Leu Ser Gln
 1               5                  10                  15

Val Asn Gly Gln Gln Val Met Gln Ile Pro Gln Tyr Gln His Val Gln
                20                  25                  30

Glu Gly Glu Asp Phe Thr Thr Tyr Cys Asn Ser Ser Thr Thr Leu Ser
            35                  40                  45

Asn Ile Gln Trp Tyr Lys Gln Arg Pro Gly Gly His Pro Val Phe Leu
 50                  55                  60

Ile Gln Leu Val Lys Ser Gly Glu Val Lys Lys Gln Lys Arg Leu Thr
 65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Asn Val Gly
            100                 105                 110

Gly Thr Gly Lys Leu Ile Phe Gly Gln Gly Thr Thr Leu Gln Val Lys
            115                 120                 125

Pro Asp Ile Gln Asn Pro Asp Pro Ala Val Tyr Gln Leu Arg Asp Xaa
            130                 135                 140
```

<210> SEQ ID NO 6
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (141)..(141)
<223> OTHER INFORMATION: Xaa can be any naturally occurring amino acid

<400> SEQUENCE: 6

```
Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
                20                  25                  30

Arg Ala Ala Asn Leu Pro Cys Asn His Ser Thr Ile Ser Gly Asn Glu
            35                  40                  45

Tyr Val Tyr Trp Tyr Arg Gln Ile His Ser Gln Gly Pro Gln Tyr Ile
        50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Gln Arg Arg Asp Thr Gly Asn
                100                 105                 110

Gln Phe Tyr Phe Gly Thr Gly Thr Ser Leu Thr Val Ile Pro Asn Ile
            115                 120                 125

Gln Asn Pro Asp Pro Ala Val Tyr Gln Leu Arg Asp Xaa
                130                 135                 140
```

<210> SEQ ID NO 7
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (151)..(151)
<223> OTHER INFORMATION: Xaa can be any naturally occurring amino acid

<400> SEQUENCE: 7

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
                20                  25                  30

Val Val Glu Lys Glu Asp Val Thr Leu Asp Cys Val Tyr Glu Thr Arg
            35                  40                  45

Asp Thr Thr Tyr Tyr Leu Phe Trp Tyr Lys Gln Pro Pro Ser Gly Glu
        50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
                100                 105                 110

Ala Leu Ser Glu Ile Lys Asn Gln Gly Gly Lys Leu Ile Phe Gly Gln
            115                 120                 125

Gly Thr Glu Leu Ser Val Lys Pro Asn Ile Gln Asn Pro Asp Pro Ala
        130                 135                 140

Val Tyr Gln Leu Arg Asp Xaa
145                 150
```

<210> SEQ ID NO 8
<211> LENGTH: 143
<212> TYPE: PRT
<213> ORGANISM: Artificial Sequence
<220> FEATURE:
<223> OTHER INFORMATION: Synthetic

```
<220> FEATURE:
<221> NAME/KEY: misc_feature
<222> LOCATION: (143)..(143)
<223> OTHER INFORMATION: Xaa can be any naturally occurring amino acid

<400> SEQUENCE: 8
```

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Gly Glu Leu Ser Phe Gly Ala Gly Thr Thr Val Thr Val Arg Ala
        115                 120                 125

Asn Ile Gln Asn Pro Asp Pro Ala Val Tyr Gln Leu Arg Asp Xaa
130                 135                 140

```
<210> SEQ ID NO 9
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 9
```

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Glu Gly Gly Ala Thr Asn Lys Leu Ile Phe Gly Thr Gly Thr
        115                 120                 125

Leu Leu Ala Val Gln Pro Asn Ile Gln Asn Pro Asp Pro Ala Val Tyr
        130                 135                 140

Gln Leu Arg Asp Xaa
145

```
<210> SEQ ID NO 10
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 10

Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Asn Ala Gly Gly Gly Ser Gln Gly Asn Leu Ile Phe Gly Lys Gly Thr
        115                 120                 125

Lys Leu Ser Val Lys Pro Asn Ile Gln Asn Pro Asp Pro Ala Val Tyr
    130                 135                 140

Gln Leu Arg Asp Xaa
145

<210> SEQ ID NO 11
<211> LENGTH: 146
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (146)..(146)
<223> OTHER INFORMATION: Xaa can be any naturally occurring amino acid

<400> SEQUENCE: 11

Met Leu Leu Leu Val Pro Ala Phe Gln Val Ile Phe Thr Leu Gly
1               5                   10                  15

Gly Thr Arg Ala Gln Ser Val Thr Gln Leu Asp Ser Gln Val Pro Val
            20                  25                  30

Phe Glu Glu Ala Pro Val Glu Leu Arg Cys Asn Tyr Ser Ser Ser Val
        35                  40                  45

Ser Val Tyr Leu Phe Trp Tyr Val Gln Tyr Pro Asn Gln Gly Leu Gln
    50                  55                  60

Leu Leu Leu Lys Tyr Leu Ser Gly Ser Thr Leu Val Lys Gly Ile Asn
65                  70                  75                  80

Gly Phe Glu Ala Glu Phe Asn Lys Ser Gln Thr Ser Phe His Leu Arg
                85                  90                  95

Lys Pro Ser Val His Ile Ser Asp Thr Ala Glu Tyr Phe Cys Ala Val
            100                 105                 110

Ser Gly Ser Gly Asp Lys Leu Ile Phe Gly Thr Gly Thr Arg Leu Gln
```

```
                115                 120                 125
Val Phe Pro Asn Ile Gln Asn Pro Asp Pro Ala Val Tyr Gln Leu Arg
    130                 135                 140

Asp Xaa
145

<210> SEQ ID NO 12
<211> LENGTH: 164
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (164)..(164)
<223> OTHER INFORMATION: Xaa can be any naturally occurring amino acid

<400> SEQUENCE: 12

Asp Gln Lys Arg Arg Leu Leu Thr Leu Gln Gln Gly Pro Val Ser Met
1               5                   10                  15

Ala Cys Pro Gly Phe Leu Trp Ala Leu Val Ile Ser Thr Cys Leu Glu
            20                  25                  30

Phe Ser Met Ala Gln Thr Val Thr Gln Ser Gln Pro Glu Met Ser Val
        35                  40                  45

Gln Glu Ala Glu Thr Val Thr Leu Ser Cys Thr Tyr Asp Thr Ser Glu
    50                  55                  60

Ser Asp Tyr Tyr Leu Phe Trp Tyr Lys Gln Pro Pro Ser Arg Gln Met
65                  70                  75                  80

Ile Leu Val Ile Arg Gln Glu Ala Tyr Lys Gln Asn Ala Thr Glu
                85                  90                  95

Asn Arg Phe Ser Val Asn Phe Gln Lys Ala Ala Lys Ser Phe Ser Leu
            100                 105                 110

Lys Ile Ser Asp Ser Gln Leu Gly Asp Ala Ala Met Tyr Phe Cys Ala
        115                 120                 125

Ser Phe Ser Gly Gly Tyr Gln Lys Val Thr Phe Gly Thr Gly Thr Lys
    130                 135                 140

Leu Gln Val Ile Pro Asn Ile Gln Asn Pro Asp Pro Ala Val Tyr Gln
145                 150                 155                 160

Leu Arg Asp Xaa

<210> SEQ ID NO 13
<211> LENGTH: 150
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (150)..(150)
<223> OTHER INFORMATION: Xaa can be any naturally occurring amino acid

<400> SEQUENCE: 13

Met Glu Thr Val Leu Gln Val Leu Leu Gly Ile Leu Gly Phe Gln Ala
1               5                   10                  15

Ala Trp Val Ser Ser Gln Glu Leu Glu Gln Ser Pro Gln Ser Leu Ile
            20                  25                  30

Val Gln Glu Gly Lys Asn Leu Thr Ile Asn Cys Thr Ser Ser Lys Thr
        35                  40                  45

Leu Tyr Gly Leu Tyr Trp Tyr Lys Gln Lys Tyr Gly Glu Gly Leu Ile
    50                  55                  60
```

```
Phe Leu Met Met Leu Gln Lys Gly Gly Glu Glu Lys Ser His Glu Lys
 65                  70                  75                  80

Ile Thr Ala Lys Leu Asp Glu Lys Lys Gln Gln Ser Ser Leu His Ile
                 85                  90                  95

Thr Ala Ser Gln Pro Ser His Ala Gly Ile Tyr Leu Cys Gly Ala Gly
            100                 105                 110

Arg Pro Asn Ser Gly Gly Ser Asn Tyr Lys Leu Thr Phe Gly Lys Gly
        115                 120                 125

Thr Leu Leu Thr Val Asn Pro Asn Ile Gln Asn Pro Asp Pro Ala Val
    130                 135                 140

Tyr Gln Leu Arg Asp Xaa
145             150

<210> SEQ ID NO 14
<211> LENGTH: 145
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (145)..(145)
<223> OTHER INFORMATION: Xaa can be any naturally occurring amino acid

<400> SEQUENCE: 14

Met Thr Ser Ile Arg Ala Val Phe Ile Phe Leu Trp Leu Gln Leu Asp
  1               5                  10                  15

Leu Val Asn Gly Glu Asn Val Glu Gln His Pro Ser Thr Leu Ser Val
                 20                  25                  30

Gln Glu Gly Asp Ser Ala Val Ile Lys Cys Thr Tyr Ser Asp Ser Ala
             35                  40                  45

Ser Asn Tyr Phe Pro Trp Tyr Lys Gln Glu Leu Gly Lys Arg Pro Gln
     50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Gly
            100                 105                 110

Gly Arg Asp Asp Lys Ile Ile Phe Gly Lys Gly Thr Arg Leu His Ile
        115                 120                 125

Leu Pro Asn Ile Gln Asn Pro Asp Pro Ala Val Tyr Gln Leu Arg Asp
    130                 135                 140

Xaa
145

<210> SEQ ID NO 15
<211> LENGTH: 144
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (144)..(144)
<223> OTHER INFORMATION: Xaa can be any naturally occurring amino acid

<400> SEQUENCE: 15

Met Trp Gly Val Phe Leu Leu Tyr Val Ser Met Lys Met Gly Gly Thr
  1               5                  10                  15
```

```
Thr Gly Gln Asn Ile Asp Gln Pro Thr Glu Met Thr Ala Thr Glu Gly
             20                  25                  30

Ala Ile Val Gln Ile Asn Cys Thr Tyr Gln Thr Ser Gly Phe Asn Gly
         35                  40                  45

Leu Phe Trp Tyr Gln Gln His Ala Gly Glu Ala Pro Thr Phe Leu Ser
 50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
             85                  90                  95

Met Lys Asp Ser Ala Ser Tyr Leu Cys Ala Val Arg Pro Ser Asn Gln
            100                 105                 110

Ala Gly Thr Ala Leu Ile Phe Gly Lys Gly Thr Thr Leu Ser Val Ser
        115                 120                 125

Ser Asn Ile Gln Asn Pro Asp Pro Ala Val Tyr Gln Leu Arg Asp Xaa
    130                 135                 140
```

<210> SEQ ID NO 16
<211> LENGTH: 147
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (147)..(147)
<223> OTHER INFORMATION: Xaa can be any naturally occurring amino acid

<400> SEQUENCE: 16

```
Met Glu Lys Asn Pro Leu Ala Ala Pro Leu Leu Ile Leu Trp Phe His
1               5                  10                  15

Leu Asp Cys Val Ser Ser Ile Leu Asn Val Glu Gln Ser Pro Gln Ser
             20                  25                  30

Leu His Val Gln Glu Gly Asp Ser Thr Asn Phe Thr Cys Ser Phe Pro
         35                  40                  45

Ser Ser Asn Phe Tyr Ala Leu His Trp Tyr Arg Trp Glu Thr Ala Lys
 50                  55                  60

Ser Pro Glu Ala Leu Phe Val Met Thr Leu Asn Gly Asp Glu Lys Lys
65                  70                  75                  80

Lys Gly Arg Ile Ser Ala Thr Leu Asn Thr Lys Glu Gly Tyr Ser Tyr
             85                  90                  95

Leu Tyr Ile Lys Gly Ser Gln Pro Glu Asp Ser Ala Thr Tyr Leu Cys
            100                 105                 110

Ala Ser Leu Tyr Phe Asn Lys Phe Tyr Phe Gly Ser Gly Thr Lys Leu
        115                 120                 125

Asn Val Lys Pro Asn Ile Gln Asn Pro Asp Pro Ala Val Tyr Gln Leu
    130                 135                 140

Arg Asp Xaa
145
```

<210> SEQ ID NO 17
<211> LENGTH: 145
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (145)..(145)

<223> OTHER INFORMATION: Xaa can be any naturally occurring amino acid

<400> SEQUENCE: 17

```
Met Thr Ser Ile Arg Ala Val Phe Ile Phe Leu Trp Leu Gln Leu Asp
1               5                   10                  15
Leu Val Asn Gly Glu Asn Val Glu Gln His Pro Ser Thr Leu Ser Val
            20                  25                  30
Gln Glu Gly Asp Ser Ala Val Ile Lys Cys Thr Tyr Ser Asp Ser Ala
        35                  40                  45
Ser Asn Tyr Phe Pro Trp Tyr Lys Gln Glu Leu Gly Lys Arg Pro Gln
    50                  55                  60
Leu Ile Ile Asp Ile Arg Ser Asn Val Gly Glu Lys Lys Asp Gln Arg
65                  70                  75                  80
Ile Ala Val Thr Leu Asn Lys Thr Ala Lys His Phe Ser Leu His Ile
                85                  90                  95
Thr Glu Thr Gln Pro Glu Asp Ser Ala Val Tyr Phe Cys Ala Ala Ile
            100                 105                 110
Gly Phe Gly Asn Val Leu His Cys Gly Ser Gly Thr Gln Val Ile Val
        115                 120                 125
Leu Pro His Ile Gln Asn Pro Asp Pro Ala Val Tyr Gln Leu Arg Asp
    130                 135                 140
Xaa
145
```

<210> SEQ ID NO 18
<211> LENGTH: 144
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (144)..(144)
<223> OTHER INFORMATION: Xaa can be any naturally occurring amino acid

<400> SEQUENCE: 18

```
Met Leu Leu Ile Thr Ser Met Leu Val Leu Trp Met Gln Leu Ser Gln
1               5                   10                  15
Val Asn Gly Gln Gln Val Met Gln Ile Pro Gln Tyr Gln His Val Gln
            20                  25                  30
Glu Gly Glu Asp Phe Thr Thr Tyr Cys Asn Ser Ser Thr Thr Leu Ser
        35                  40                  45
Asn Ile Gln Trp Tyr Lys Gln Arg Pro Gly Gly His Pro Val Phe Leu
    50                  55                  60
Ile Gln Leu Val Lys Ser Gly Glu Val Lys Lys Gln Lys Arg Leu Thr
65                  70                  75                  80
Phe Gln Phe Gly Glu Ala Lys Lys Asn Ser Ser Leu His Ile Thr Ala
                85                  90                  95
Thr Gln Thr Thr Asp Val Gly Thr Tyr Phe Cys Ala Gly Ala Pro Ser
            100                 105                 110
Asn Asp Tyr Lys Leu Ser Phe Gly Ala Gly Thr Thr Val Thr Val Arg
        115                 120                 125
Ala Asn Ile Gln Asn Pro Asp Pro Ala Val Tyr Gln Leu Arg Asp Xaa
    130                 135                 140
```

<210> SEQ ID NO 19
<211> LENGTH: 142
<212> TYPE: PRT

```
<213> ORGANISM: Artificial Sequence
<220> FEATURE:
<223> OTHER INFORMATION: Synthetic
<220> FEATURE:
<221> NAME/KEY: misc_feature
<222> LOCATION: (142)..(142)
<223> OTHER INFORMATION: Xaa can be any naturally occurring amino acid

<400> SEQUENCE: 19

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Ala Asp Asn
            100                 105                 110

Asn Asp Met Arg Phe Gly Ala Gly Thr Arg Leu Thr Val Lys Pro Asn
        115                 120                 125

Ile Gln Asn Pro Asp Pro Ala Val Tyr Gln Leu Arg Asp Xaa
    130                 135                 140

<210> SEQ ID NO 20
<211> LENGTH: 144
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (144)..(144)
<223> OTHER INFORMATION: Xaa can be any naturally occurring amino acid

<400> SEQUENCE: 20

Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Gly Thr Ser Asn Phe
            100                 105                 110

Gly Asn Glu Lys Leu Thr Phe Gly Thr Gly Thr Arg Leu Thr Ile Ile
        115                 120                 125

Pro Asn Ile Gln Asn Pro Asp Pro Ala Val Tyr Gln Leu Arg Asp Xaa
    130                 135                 140
```

```
<210> SEQ ID NO 21
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 21

Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Asn Asp Ser Gly Gly Gly Ala Asp Gly Leu Thr Phe Gly Lys Gly Thr
        115                 120                 125

His Leu Ile Ile Gln Pro Tyr Ile Gln Asn Pro Asp Pro Ala Val Tyr
    130                 135                 140

Gln Leu Arg Asp Xaa
145

<210> SEQ ID NO 22
<211> LENGTH: 146
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (146)..(146)
<223> OTHER INFORMATION: Xaa can be any naturally occurring amino acid

<400> SEQUENCE: 22

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Met
            100                 105                 110

Arg Gly Gly Ala Asp Gly Leu Thr Phe Gly Lys Gly Thr His Leu Ile
```

```
                115                 120                 125
Ile Gln Pro Tyr Ile Gln Asn Pro Asp Pro Ala Val Tyr Gln Leu Arg
    130                 135                 140

Asp Xaa
145

<210> SEQ ID NO 23
<211> LENGTH: 145
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (145)..(145)
<223> OTHER INFORMATION: Xaa can be any naturally occurring amino acid

<400> SEQUENCE: 23

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Thr
            100                 105                 110

Gly Gly Ala Asp Gly Leu Thr Phe Gly Lys Gly Thr His Leu Ile Ile
        115                 120                 125

Gln Pro Tyr Ile Gln Asn Pro Asp Pro Ala Val Tyr Gln Leu Arg Asp
    130                 135                 140

Xaa
145

<210> SEQ ID NO 24
<211> LENGTH: 139
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (139)..(139)
<223> OTHER INFORMATION: Xaa can be any naturally occurring amino acid

<400> SEQUENCE: 24

Met Trp Gly Ala Phe Leu Leu Tyr Val Ser Met Lys Met Gly Gly Thr
1               5                   10                  15

Ala Gly Gln Ser Leu Glu Gln Pro Ser Glu Val Thr Ala Val Glu Gly
                20                  25                  30

Ala Ile Val Gln Ile Asn Cys Thr Tyr Gln Thr Ser Gly Phe Tyr Gly
            35                  40                  45

Leu Ser Trp Tyr Gln Gln His Asp Gly Gly Ala Pro Thr Phe Leu Ser
    50                  55                  60

Tyr Asn Ala Leu Asp Gly Leu Glu Glu Thr Gly Arg Phe Ser Ser Phe
```

```
                65                  70                  75                  80
Leu Ser Arg Ser Asp Ser Tyr Gly Tyr Leu Leu Gln Glu Leu Gln
                    85                  90                  95

Met Lys Asp Ser Ala Ser Tyr Phe Cys Ala Asp Gln Gly Gly Lys Leu
                    100                 105                 110

Ile Phe Gly Gln Gly Thr Glu Leu Ser Val Lys Pro Asn Ile Gln Asn
                    115                 120                 125

Pro Asp Pro Ala Val Tyr Gln Leu Arg Asp Xaa
                    130                 135

<210> SEQ ID NO 25
<211> LENGTH: 147
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (147)..(147)
<223> OTHER INFORMATION: Xaa can be any naturally occurring amino acid

<400> SEQUENCE: 25

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys
            50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                    85                  90                  95

Phe Ile Arg Asp Ser Gln Pro Ser Asp Ser Ala Thr Tyr Leu Cys Ala
                    100                 105                 110

Met Lys Thr Ser Tyr Asp Lys Val Ile Phe Gly Pro Gly Thr Ser Leu
                    115                 120                 125

Ser Val Ile Pro Asn Ile Gln Asn Pro Asp Pro Ala Val Tyr Gln Leu
                    130                 135                 140

Arg Asp Xaa
145

<210> SEQ ID NO 26
<211> LENGTH: 144
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (144)..(144)
<223> OTHER INFORMATION: Xaa can be any naturally occurring amino acid

<400> SEQUENCE: 26

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
                20                  25                  30

Glu Gly Glu Asn Leu Thr Val Tyr Cys Asn Ser Ser Ser Val Phe Ser
```

```
                35                  40                  45
Ser Leu Gln Trp Tyr Arg Gln Glu Pro Gly Glu Gly Pro Val Leu Leu
 50                  55                  60

Val Thr Val Thr Gly Gly Glu Val Lys Lys Leu Lys Arg Leu Thr
 65                  70                  75                  80

Phe Gln Phe Gly Asp Ala Arg Lys Asp Ser Leu His Ile Thr Ala
                 85                  90                  95

Ala Gln Pro Gly Asp Thr Gly Leu Tyr Leu Cys Ala Ala Ser Gly Gly
                100                 105                 110

Ser Asn Tyr Lys Leu Thr Phe Gly Lys Gly Thr Leu Thr Val Asn
                115                 120                 125

Pro Asn Ile Gln Asn Pro Asp Pro Ala Val Tyr Gln Leu Arg Asp Xaa
                130                 135                 140
```

<210> SEQ ID NO 27
<211> LENGTH: 147
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (147)..(147)
<223> OTHER INFORMATION: Xaa can be any naturally occurring amino acid

<400> SEQUENCE: 27

```
Met Ile Ser Leu Arg Val Leu Leu Val Ile Leu Trp Leu Gln Leu Ser
 1               5                  10                  15

Trp Val Trp Ser Gln Arg Lys Glu Val Glu Gln Asp Pro Gly Pro Phe
                20                  25                  30

Asn Val Pro Glu Gly Ala Thr Val Ala Phe Asn Cys Thr Tyr Ser Asn
                35                  40                  45

Ser Ala Ser Gln Ser Phe Phe Trp Tyr Arg Gln Asp Cys Arg Lys Glu
 50                  55                  60

Pro Lys Leu Leu Met Ser Val Tyr Ser Ser Gly Asn Glu Asp Gly Arg
 65                  70                  75                  80

Phe Thr Ala Gln Leu Asn Arg Ala Ser Gln Tyr Ile Ser Leu Leu Ile
                 85                  90                  95

Arg Asp Ser Lys Leu Ser Asp Ser Ala Thr Tyr Leu Cys Ala Val Asn
                100                 105                 110

Pro Ser Arg Gly Tyr Ser Thr Leu Thr Phe Gly Lys Gly Thr Met Leu
                115                 120                 125

Leu Val Ser Pro Asp Ile Gln Asn Pro Asp Pro Ala Val Tyr Gln Leu
                130                 135                 140

Arg Asp Xaa
145
```

<210> SEQ ID NO 28
<211> LENGTH: 144
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (144)..(144)
<223> OTHER INFORMATION: Xaa can be any naturally occurring amino acid

<400> SEQUENCE: 28

Met Glu Thr Leu Leu Gly Leu Leu Ile Leu Trp Leu Gln Leu Gln Trp

```
            1               5                  10                 15
Val Ser Ser Lys Gln Glu Val Thr Gln Ile Pro Ala Ala Leu Ser Val
            20                 25                 30

Pro Glu Gly Glu Asn Leu Val Leu Asn Cys Ser Phe Thr Asp Ser Ala
            35                 40                 45

Ile Tyr Asn Leu Gln Trp Phe Arg Gln Asp Pro Gly Lys Gly Leu Thr
        50                 55                 60

Ser Leu Leu Leu Ile Gln Ser Ser Gln Arg Glu Gln Thr Ser Gly Arg
65                 70                 75                 80

Leu Asn Ala Ser Leu Asp Lys Ser Ser Gly Arg Ser Thr Leu Tyr Ile
                    85                 90                 95

Ala Ala Ser Gln Pro Gly Asp Ser Ala Thr Tyr Leu Cys Ala Val Tyr
                100                105                110

Gly Asn Asn Arg Leu Ala Phe Gly Lys Gly Asn Gln Val Val Val Ile
                115                120                125

Pro Asn Ile Gln Asn Pro Asp Pro Ala Val Tyr Gln Leu Arg Asp Xaa
                130                135                140

<210> SEQ ID NO 29
<211> LENGTH: 146
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (146)..(146)
<223> OTHER INFORMATION: Xaa can be any naturally occurring amino acid

<400> SEQUENCE: 29

Met Leu Leu Glu Leu Ile Pro Leu Leu Gly Ile His Phe Val Leu Arg
1               5                  10                 15

Thr Ala Arg Ala Gln Ser Val Thr Gln Pro Asp Ile His Ile Thr Val
            20                 25                 30

Ser Glu Gly Ala Ser Leu Glu Leu Arg Cys Asn Tyr Ser Tyr Gly Ala
            35                 40                 45

Thr Pro Tyr Leu Phe Trp Tyr Val Gln Ser Pro Gly Gln Gly Leu Gln
        50                 55                 60

Leu Leu Leu Lys Tyr Phe Ser Gly Asp Thr Leu Val Gln Gly Ile Lys
65                 70                 75                 80

Gly Phe Glu Ala Glu Phe Lys Arg Ser Gln Ser Ser Phe Asn Leu Arg
                    85                 90                 95

Lys Pro Ser Val His Trp Ser Asp Ala Ala Glu Tyr Phe Cys Ala Val
                100                105                110

Gly Tyr Gly Asn Asn Arg Leu Ala Phe Gly Lys Gly Asn Gln Val Val
                115                120                125

Val Ile Pro Asn Ile Gln Asn Pro Asp Pro Ala Val Tyr Gln Leu Arg
                130                135                140

Asp Xaa
145

<210> SEQ ID NO 30
<211> LENGTH: 147
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (147)..(147)
<223> OTHER INFORMATION: Xaa can be any naturally occurring amino acid

<400> SEQUENCE: 30

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys Phe Ser Leu His Ile
                85                  90                  95

Thr Glu Thr Gln Pro Glu Asp Ser Ala Val Tyr Phe Cys Ala Ala Gly
            100                 105                 110

Pro Ser Asn Thr Gly Asn Gln Phe Tyr Phe Gly Thr Gly Thr Ser Leu
        115                 120                 125

Thr Val Ile Pro Asn Ile Gln Asn Pro Asp Pro Ala Val Tyr Gln Leu
    130                 135                 140

Arg Asp Xaa
145

<210> SEQ ID NO 31
<211> LENGTH: 160
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (160)..(160)
<223> OTHER INFORMATION: Xaa can be any naturally occurring amino acid

<400> SEQUENCE: 31

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser His Asn Gly Leu Gly Gln Gly Glu Asp Leu Leu Ser Gly Ala
        115                 120                 125

Asn Val Leu Thr Phe Gly Ala Gly Ser Arg Leu Thr Val Leu Glu Asp
    130                 135                 140

Leu Lys Asn Val Phe Pro Pro Glu Val Ala Val Phe Glu Pro Ser Xaa
145                 150                 155                 160
```

<210> SEQ ID NO 32
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 32

Met Ser Asn Gln Val Leu Cys Cys Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Pro Gly Gly Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Xaa
145

<210> SEQ ID NO 33
<211> LENGTH: 154
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (154)..(154)
<223> OTHER INFORMATION: Xaa can be any naturally occurring amino acid

<400> SEQUENCE: 33

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Val Asn Pro Ala Val Ser Tyr Asn Glu Gln Phe Phe Gly
            115                 120                 125

Pro Gly Thr Arg Leu Thr Val Leu Glu Asp Leu Lys Asn Val Phe Pro
    130                 135                 140

Pro Glu Val Ala Val Phe Glu Pro Ser Xaa
145                 150

<210> SEQ ID NO 34
<211> LENGTH: 132
<212> TYPE: PRT
<213> ORGANISM: Artificial Sequence
<220> FEATURE:
<223> OTHER INFORMATION: Synthetic

<400> SEQUENCE: 34

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Ala Pro Gly Tyr Asn Glu Gln Phe Phe Gly Pro Gly Thr Arg
        115                 120                 125

Leu Thr Val Leu
    130

<210> SEQ ID NO 35
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (151)..(151)
<223> OTHER INFORMATION: Xaa can be any naturally occurring amino acid

<400> SEQUENCE: 35

Met Leu Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Phe

```
                    100                 105                 110
Ile Pro Thr Gly Leu Gly Glu Asn Thr Ile Tyr Phe Gly Glu Gly Ser
                115                 120                 125

Trp Leu Thr Val Val Glu Asp Leu Asn Lys Val Phe Pro Pro Glu Val
        130                 135                 140

Ala Val Phe Glu Pro Ser Xaa
145                 150

<210> SEQ ID NO 36
<211> LENGTH: 152
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (152)..(152)
<223> OTHER INFORMATION: Xaa can be any naturally occurring amino acid

<400> SEQUENCE: 36

Met Gly Pro Gly Leu Leu Cys Trp Val Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln His Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Arg Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
                100                 105                 110

Ser Leu Thr Ala Gly Ala Tyr Thr Gly Glu Leu Phe Phe Gly Glu Gly
            115                 120                 125

Ser Arg Leu Thr Val Leu Glu Asp Leu Lys Asn Val Phe Pro Pro Glu
        130                 135                 140

Val Ala Val Phe Glu Pro Ser Xaa
145                 150

<210> SEQ ID NO 37
<211> LENGTH: 154
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (154)..(154)
<223> OTHER INFORMATION: Xaa can be any naturally occurring amino acid

<400> SEQUENCE: 37

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
```

```
                    50                  55                  60
Met Phe Val Tyr Ser Tyr Glu Lys Leu Ser Ile Asn Glu Ser Val Pro
 65                  70                  75                  80

Ser Arg Phe Ser Pro Glu Cys Pro Asn Ser Ser Leu Leu Asn Leu His
                     85                  90                  95

Leu His Ala Leu Gln Pro Glu Asp Ser Ala Leu Tyr Leu Cys Ala Ser
                    100                 105                 110

Ser Gln Gly Val Glu Arg Gln Gly Pro Arg Asn Glu Gln Phe Phe Gly
                    115                 120                 125

Pro Gly Thr Arg Leu Thr Val Leu Glu Asp Leu Lys Asn Val Phe Pro
130                 135                 140

Pro Glu Val Ala Val Phe Glu Pro Ser Xaa
145                 150
```

<210> SEQ ID NO 38
<211> LENGTH: 150
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (150)..(150)
<223> OTHER INFORMATION: Xaa can be any naturally occurring amino acid

<400> SEQUENCE: 38

```
Met Gly Pro Gln Leu Leu Gly Tyr Val Val Leu Cys Leu Leu Gly Ala
  1               5                  10                  15

Gly Pro Leu Glu Ala Gln Val Thr Gln Asn Pro Arg Tyr Leu Ile Thr
                 20                  25                  30

Val Thr Gly Lys Lys Leu Thr Val Thr Cys Ser Gln Asn Met Asn His
                 35                  40                  45

Glu Tyr Met Ser Trp Tyr Arg Gln Asp Pro Gly Leu Gly Leu Arg Gln
 50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
                100                 105                 110

Ser Ser Ser Gly Arg Asn Asn Glu Gln Phe Phe Gly Pro Gly Thr Arg
                115                 120                 125

Leu Thr Val Leu Glu Asp Leu Lys Asn Val Phe Pro Pro Glu Val Ala
130                 135                 140

Val Phe Glu Pro Ser Xaa
145                 150
```

<210> SEQ ID NO 39
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 39

```
Met Ser Asn Gln Val Leu Cys Cys Val Val Leu Cys Phe Leu Gly Ala
  1               5                  10                  15
```

```
                1               5                  10                 15
Asn Thr Val Asp Gly Gly Ile Thr Gln Ser Pro Lys Tyr Leu Phe Arg
                20                 25                 30
Lys Glu Gly Gln Asn Val Thr Leu Ser Cys Glu Gln Asn Leu Asn His
                35                 40                 45
Asp Ala Met Tyr Trp Tyr Arg Gln Asp Pro Gly Gln Gly Leu Arg Leu
    50                 55                 60
Ile Tyr Tyr Ser Gln Ile Val Asn Asp Phe Gln Lys Gly Asp Ile Ala
 65                 70                 75                 80
Glu Gly Tyr Ser Val Ser Arg Glu Lys Lys Glu Ser Phe Pro Leu Thr
                85                 90                 95
Val Thr Ser Ala Gln Lys Asn Pro Thr Ala Phe Tyr Leu Cys Ala Ser
                100                105                110
Ser Ile Ala His Gly Asp Glu Tyr Phe Gly Pro Gly Thr Arg Leu
                115                120                125
Thr Val Thr Glu Asp Leu Lys Asn Val Phe Pro Pro Glu Val Ala Val
    130                135                140
Phe Glu Pro Ser Xaa
145
```

<210> SEQ ID NO 40
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (151)..(151)
<223> OTHER INFORMATION: Xaa can be any naturally occurring amino acid

<400> SEQUENCE: 40

```
                1               5                  10                 15
Met Gly Cys Arg Leu Leu Cys Cys Ala Val Leu Cys Leu Leu Gly Ala
                20                 25                 30
Val Pro Ile Asp Thr Glu Val Thr Gln Thr Pro Lys His Leu Val Met
                35                 40                 45
Gly Met Thr Asn Lys Lys Ser Leu Lys Cys Glu Gln His Met Gly His
                50                 55                 60
Arg Ala Met Tyr Trp Tyr Lys Gln Lys Ala Lys Lys Pro Pro Glu Leu
 65                 70                 75                 80
Met Phe Val Tyr Ser Tyr Glu Lys Leu Ser Ile Asn Glu Ser Val Pro
                85                 90                 95
Ser Arg Phe Ser Pro Glu Cys Pro Asn Ser Ser Leu Leu Asn Leu His
                100                105                110
Leu His Ala Leu Gln Pro Glu Asp Ser Ala Leu Tyr Leu Cys Ala Ser
                115                120                125
Gln Asp Tyr Leu Asn Ser Tyr Asn Glu Gln Phe Phe Gly Pro Gly Thr
    130                135                140
Arg Leu Thr Val Leu Glu Asp Leu Lys Asn Val Phe Pro Pro Glu Val
145                 150
Ala Val Phe Glu Pro Ser Xaa
145                 150
```

<210> SEQ ID NO 41
<211> LENGTH: 154
<212> TYPE: PRT
<213> ORGANISM: Artificial Sequence
<220> FEATURE:

```
<223> OTHER INFORMATION: Synthetic
<220> FEATURE:
<221> NAME/KEY: misc_feature
<222> LOCATION: (154)..(154)
<223> OTHER INFORMATION: Xaa can be any naturally occurring amino acid

<400> SEQUENCE: 41

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Ala Arg Gln Gly Val Asp Gln Glu Thr Gln Tyr Phe Gly
        115                 120                 125

Pro Gly Thr Arg Leu Leu Val Leu Glu Asp Leu Lys Asn Val Phe Pro
    130                 135                 140

Pro Glu Val Ala Val Phe Glu Pro Ser Xaa
145                 150

<210> SEQ ID NO 42
<211> LENGTH: 161
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (161)..(161)
<223> OTHER INFORMATION: Xaa can be any naturally occurring amino acid

<400> SEQUENCE: 42

Arg Pro His Leu Arg Pro Glu Ala Ser Met Gly Cys Arg Leu Leu Cys
1               5                   10                  15

Cys Ala Val Leu Cys Leu Leu Gly Ala Val Pro Ile Asp Thr Glu Val
            20                  25                  30

Thr Gln Thr Pro Lys His Leu Val Met Gly Met Thr Asn Lys Lys Ser
        35                  40                  45

Leu Lys Cys Glu Gln His Met Gly His Arg Ala Met Tyr Trp Tyr Lys
    50                  55                  60

Gln Lys Ala Lys Lys Pro Pro Glu Leu Met Phe Val Tyr Ser Tyr Glu
65                  70                  75                  80

Lys Leu Ser Ile Asn Glu Ser Val Pro Ser Arg Phe Ser Pro Glu Cys
                85                  90                  95

Pro Asn Ser Ser Leu Leu Asn Leu His Leu His Ala Leu Gln Pro Glu
            100                 105                 110

Asp Ser Ala Leu Tyr Leu Cys Ala Ser Ser Gln Asp Lys Tyr Arg Gly
        115                 120                 125

Asn Glu Lys Leu Phe Phe Gly Ser Gly Thr Gln Leu Ser Val Leu Glu
    130                 135                 140
```

```
Asp Leu Asn Lys Val Phe Pro Pro Glu Val Ala Val Phe Glu Pro Ser
145                 150                 155                 160

Xaa

<210> SEQ ID NO 43
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 43

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
                35                  40                  45

Asn Ala Met Tyr Trp Tyr Lys Gln Ser Ala Lys Lys Pro Leu Glu Leu
        50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Gln Asp Arg Ala Asp Thr Gln Tyr Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Xaa
145

<210> SEQ ID NO 44
<211> LENGTH: 150
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (150)..(150)
<223> OTHER INFORMATION: Xaa can be any naturally occurring amino acid

<400> SEQUENCE: 44

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
                35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
```

```
                85                  90                  95
Leu Glu Ser Pro Ser Pro Asn Gln Thr Ser Leu Tyr Phe Cys Ala Ser
            100                 105                 110

Ser Leu Gly Gly Ser Arg Leu Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Xaa
145                 150

<210> SEQ ID NO 45
<211> LENGTH: 152
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (152)..(152)
<223> OTHER INFORMATION: Xaa can be any naturally occurring amino acid

<400> SEQUENCE: 45

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Pro Leu Asp Arg Gly Leu Ser Gly Glu Leu Phe Phe Gly Glu Gly
        115                 120                 125

Ser Arg Leu Thr Val Leu Glu Asp Leu Lys Asn Val Phe Pro Pro Glu
    130                 135                 140

Val Ala Val Phe Glu Pro Ser Xaa
145                 150

<210> SEQ ID NO 46
<211> LENGTH: 152
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (152)..(152)
<223> OTHER INFORMATION: Xaa can be any naturally occurring amino acid

<400> SEQUENCE: 46

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
```

```
                35                  40                  45
Glu Tyr Met Ser Trp Tyr Arg Gln Asp Pro Gly Leu Gly Leu Arg Gln
 50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
                100                 105                 110

Ser Leu Ser Phe Gly Ser Gly Ala Asn Val Leu Thr Phe Gly Ala Gly
                115                 120                 125

Ser Arg Leu Thr Val Leu Glu Asp Leu Lys Asn Val Phe Pro Pro Glu
                130                 135                 140

Val Ala Val Phe Glu Pro Ser Xaa
145                 150
```

<210> SEQ ID NO 47
<211> LENGTH: 150
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (150)..(150)
<223> OTHER INFORMATION: Xaa can be any naturally occurring amino acid

<400> SEQUENCE: 47

```
Met Ser Leu Gly Leu Leu Cys Cys Gly Ala Phe Ser Leu Leu Trp Ala
 1               5                  10                  15

Gly Pro Val Asn Ala Gly Val Thr Gln Thr Pro Lys Phe Arg Val Leu
                 20                  25                  30

Lys Thr Gly Gln Ser Met Thr Leu Leu Cys Ala Gln Asp Met Asn His
                 35                  40                  45

Glu Tyr Met Tyr Trp Tyr Arg Gln Asp Pro Gly Met Gly Leu Arg Leu
 50                  55                  60

Ile His Tyr Ser Val Gly Glu Gly Thr Thr Ala Lys Gly Glu Val Pro
 65                  70                  75                  80

Asp Gly Tyr Asn Val Ser Arg Leu Lys Lys Gln Asn Phe Leu Leu Gly
                 85                  90                  95

Leu Glu Ser Ala Ala Pro Ser Gln Thr Ser Val Tyr Phe Cys Ala Ser
                100                 105                 110

Ser Tyr Thr Ser Asn Thr Gly Glu Leu Phe Phe Gly Glu Gly Ser Arg
                115                 120                 125

Leu Thr Val Leu Glu Asp Leu Lys Asn Val Phe Pro Pro Glu Val Ala
                130                 135                 140

Val Phe Glu Pro Ser Xaa
145                 150
```

<210> SEQ ID NO 48
<211> LENGTH: 148
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (148)..(148)
<223> OTHER INFORMATION: Xaa can be any naturally occurring amino acid

```
<400> SEQUENCE: 48

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Gly
            100                 105                 110

Tyr Gly Gln Gly Pro Glu Gln Tyr Phe Gly Pro Gly Thr Arg Leu Thr
        115                 120                 125

Val Thr Glu Asp Leu Lys Asn Val Phe Pro Pro Glu Val Ala Val Phe
    130                 135                 140

Glu Pro Ser Xaa
145

<210> SEQ ID NO 49
<211> LENGTH: 152
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (152)..(152)
<223> OTHER INFORMATION: Xaa can be any naturally occurring amino acid

<400> SEQUENCE: 49

Met Gly Pro Arg Leu Leu Phe Trp Ala Leu Leu Cys Leu Leu Gly Thr
1               5                   10                  15

Gly Pro Val Glu Ala Gly Val Thr Gln Ser Pro Thr His Leu Ile Lys
            20                  25                  30

Thr Arg Gly Gln Gln Ala Thr Leu Arg Cys Ser Pro Ile Ser Gly His
        35                  40                  45

Thr Ser Val Tyr Trp Tyr Gln Gln Ala Leu Gly Leu Gly Leu Gln Phe
    50                  55                  60

Leu Leu Trp Tyr Asp Glu Gly Glu Glu Arg Asn Arg Gly Asn Phe Pro
65                  70                  75                  80

Pro Arg Phe Ser Gly Arg Gln Phe Pro Asn Tyr Ser Ser Glu Leu Asn
                85                  90                  95

Val Asn Ala Leu Glu Leu Glu Asp Ser Ala Leu Tyr Leu Cys Ala Ser
            100                 105                 110

Ser Pro Gly Thr Pro Phe Ser Tyr Asn Glu Gln Phe Phe Gly Pro Gly
        115                 120                 125

Thr Arg Leu Thr Val Leu Glu Asp Leu Lys Asn Val Phe Pro Pro Glu
    130                 135                 140

Val Ala Val Phe Glu Pro Ser Xaa
145                 150

<210> SEQ ID NO 50
<211> LENGTH: 150
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (150)..(150)
<223> OTHER INFORMATION: Xaa can be any naturally occurring amino acid

<400> SEQUENCE: 50

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Phe Ala Val Tyr Gly Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Xaa
145                 150

<210> SEQ ID NO 51
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (151)..(151)
<223> OTHER INFORMATION: Xaa can be any naturally occurring amino acid

<400> SEQUENCE: 51

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Thr Leu Ala Gly Thr Tyr Asn Glu Gln Phe Phe Gly Pro Gly Thr
        115                 120                 125
```

Arg Leu Thr Val Leu Glu Asp Leu Lys Asn Val Phe Pro Pro Glu Val
    130                 135                 140

Ala Val Phe Glu Pro Ser Xaa
145                 150

<210> SEQ ID NO 52
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (151)..(151)
<223> OTHER INFORMATION: Xaa can be any naturally occurring amino acid

<400> SEQUENCE: 52

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Pro Pro Gly Gly Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Xaa
145                 150

<210> SEQ ID NO 53
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 53

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

```
Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Ser Asn Ala Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Xaa
145

<210> SEQ ID NO 54
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (151)..(151)
<223> OTHER INFORMATION: Xaa can be any naturally occurring amino acid

<400> SEQUENCE: 54

Met Arg Ile Arg Leu Leu Cys Cys Val Ala Phe Ser Leu Leu Trp Ala
1               5                   10                  15

Gly Pro Val Ile Ala Gly Ile Thr Gln Ala Pro Thr Ser Gln Ile Leu
            20                  25                  30

Ala Ala Gly Arg Arg Met Thr Leu Arg Cys Thr Gln Asp Met Arg His
        35                  40                  45

Asn Ala Met Tyr Trp Tyr Arg Gln Asp Leu Gly Leu Gly Leu Arg Leu
    50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

Ser Leu Gly Leu Ala Gly Asp Asp Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Xaa
145                 150

<210> SEQ ID NO 55
<211> LENGTH: 147
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (147)..(147)
<223> OTHER INFORMATION: Xaa can be any naturally occurring amino acid

<400> SEQUENCE: 55

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30
```

```
Gly Thr Gly Lys Lys Ile Thr Leu Glu Cys Ser Gln Thr Met Gly His
            35                  40                  45

Asp Lys Met Tyr Trp Tyr Gln Gln Asp Pro Gly Met Glu Leu His Leu
 50                  55                  60

Ile His Tyr Ser Tyr Gly Val Asn Ser Thr Glu Lys Gly Asp Leu Ser
 65                  70                  75                  80

Ser Glu Ser Thr Val Ser Arg Ile Arg Thr Glu His Phe Pro Leu Thr
                 85                  90                  95

Leu Glu Ser Ala Arg Pro Ser His Thr Ser Gln Tyr Leu Cys Ala Ser
                100                 105                 110

Ser Arg Gly Asp Glu Gln Phe Phe Gly Pro Gly Thr Arg Leu Thr Val
                115                 120                 125

Leu Glu Asp Leu Lys Asn Val Phe Pro Pro Glu Val Ala Val Phe Glu
            130                 135                 140

Pro Ser Xaa
145

<210> SEQ ID NO 56
<211> LENGTH: 151
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (151)..(151)
<223> OTHER INFORMATION: Xaa can be any naturally occurring amino acid

<400> SEQUENCE: 56

Met Gly Ile Arg Leu Leu Cys Arg Val Ala Phe Cys Phe Leu Ala Val
 1               5                  10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
 50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Ser
                100                 105                 110

Ile Gly Glu Thr Gly Phe Val Glu Thr Gln Tyr Phe Gly Pro Gly Thr
            115                 120                 125

Arg Leu Leu Val Leu Glu Asp Leu Lys Asn Val Phe Pro Pro Glu Val
            130                 135                 140

Ala Val Phe Glu Pro Ser Xaa
145                 150

<210> SEQ ID NO 57
<211> LENGTH: 150
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (150)..(150)
<223> OTHER INFORMATION: Xaa can be any naturally occurring amino acid
```

<400> SEQUENCE: 57

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Glu Thr Gly Ile Arg Asp Gly Tyr Thr Phe Gly Ser Gly Thr Arg
        115                 120                 125

Leu Thr Val Val Glu Asp Leu Asn Lys Val Phe Pro Pro Glu Val Ala
    130                 135                 140

Val Phe Glu Pro Ser Xaa
145             150
```

<210> SEQ ID NO 58
<211> LENGTH: 153
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (153)..(153)
<223> OTHER INFORMATION: Xaa can be any naturally occurring amino acid

<400> SEQUENCE: 58

```
Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Asp Pro Ser Asp Arg Val Gly Gln Glu Thr Gln Tyr Phe Gly Pro
        115                 120                 125

Gly Thr Arg Leu Leu Val Leu Glu Asp Leu Lys Asn Val Phe Pro Pro
    130                 135                 140

Glu Val Ala Val Phe Glu Pro Ser Xaa
145                 150
```

<210> SEQ ID NO 59

```
<211> LENGTH: 149
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (149)..(149)
<223> OTHER INFORMATION: Xaa can be any naturally occurring amino acid

<400> SEQUENCE: 59

Met Gly Ser Arg Leu Leu Cys Trp Val Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Leu Glu Gly Ser Arg Gly Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Xaa
145

<210> SEQ ID NO 60
<211> LENGTH: 153
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (153)..(153)
<223> OTHER INFORMATION: Xaa can be any naturally occurring amino acid

<400> SEQUENCE: 60

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Leu His Ile Ala Gly Gly Ile Ser Asp Thr Gln Tyr Phe Gly Pro
        115                 120                 125
```

Gly Thr Arg Leu Thr Val Leu Glu Asp Leu Lys Asn Val Phe Pro Pro
    130                 135                 140

Glu Val Ala Val Phe Glu Pro Ser Xaa
145                 150

<210> SEQ ID NO 61
<211> LENGTH: 5
<212> TYPE: PRT
<213> ORGANISM: Artificial Sequence
<220> FEATURE:
<223> OTHER INFORMATION: Synthetic

<400> SEQUENCE: 61

Ser Val Phe Ser Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic

<400> SEQUENCE: 62

Ser Ile Phe Asn Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Thr Ser Glu Ser Asn Tyr Tyr
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic

<400> SEQUENCE: 64

Thr Ser Glu Asn Asn Tyr Tyr
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic

<400> SEQUENCE: 65

Thr Thr Leu Ser Asn
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

Thr Ile Ser Gly Asn Glu Tyr
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic

<400> SEQUENCE: 67

Thr Arg Asp Thr Thr Tyr Tyr
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic

<400> SEQUENCE: 68

Asp Ser Ala Ile Tyr Asn
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic

<400> SEQUENCE: 69

Val Ser Gly Asn Pro Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic

<400> SEQUENCE: 70

Tyr Gly Gly Thr Val Asn
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic

<400> SEQUENCE: 71

Ser Ser Val Ser Val Tyr
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic

```
<400> SEQUENCE: 72

Thr Ser Glu Ser Asp Tyr Tyr
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic

<400> SEQUENCE: 73

Lys Thr Leu Tyr Gly
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic

<400> SEQUENCE: 74

Asp Ser Ala Ser Asn Tyr
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic

<400> SEQUENCE: 75

Thr Ser Gly Phe Asn Gly
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Ser Ser Asn Phe Tyr Ala
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic

<400> SEQUENCE: 77

Asp Ser Ala Ser Asn Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic

<400> SEQUENCE: 78
```

Thr Thr Leu Ser Asn
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic

<400> SEQUENCE: 79

Ser Val Phe Ser Ser
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic

<400> SEQUENCE: 80

Thr Thr Leu Ser Asn
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic

<400> SEQUENCE: 81

Asn Ser Ala Ser Asp Tyr
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic

<400> SEQUENCE: 82

Asp Ser Ala Ser Asn Tyr
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic

<400> SEQUENCE: 83

Asp Ser Ala Ile Tyr Asn
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic

<400> SEQUENCE: 84

Thr Ser Gly Phe Tyr Gly
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic

<400> SEQUENCE: 85

Asn Ser Ala Phe Gln Tyr
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic

<400> SEQUENCE: 86

Ser Val Phe Ser Ser
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic

<400> SEQUENCE: 87

Asn Ser Ala Ser Gln Ser
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic

<400> SEQUENCE: 88

Asp Ser Ala Ile Tyr Asn
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic

<400> SEQUENCE: 89

Tyr Gly Ala Thr Pro Tyr
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic

<400> SEQUENCE: 90

Asp Ser Ala Ser Asn Tyr

```
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic

<400> SEQUENCE: 91

Val Val Thr Gly Gly Glu Val
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic

<400> SEQUENCE: 92

Leu Tyr Lys Ala Gly Glu Leu
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic

<400> SEQUENCE: 93

Gln Glu Ala Tyr Lys Gln Gln Asn
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic

<400> SEQUENCE: 94

Gln Glu Ala Tyr Lys Gln Gln Asn
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

Leu Val Lys Ser Gly Glu Val
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic

<400> SEQUENCE: 96

Gly Leu Lys Asn Asn
1               5
```

```
<210> SEQ ID NO 97
<211> LENGTH: 8
<212> TYPE: PRT
<213> ORGANISM: Artificial Sequence
<220> FEATURE:
<223> OTHER INFORMATION: Synthetic

<400> SEQUENCE: 97

Arg Asn Ser Phe Asp Glu Gln Asn
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Ile Gln Ser Ser Gln Arg Glu
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic

<400> SEQUENCE: 99

Tyr Ile Thr Gly Asp Asn Leu Val
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Tyr Phe Ser Gly Asp Pro Leu Val
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic

<400> SEQUENCE: 101

Tyr Leu Ser Gly Ser Thr Leu Val
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Gln Glu Ala Tyr Lys Gln Gln Asn
1               5
```

```
<210> SEQ ID NO 103
<211> LENGTH: 7
<212> TYPE: PRT
<213> ORGANISM: Artificial Sequence
<220> FEATURE:
<223> OTHER INFORMATION: Synthetic

<400> SEQUENCE: 103

Leu Gln Lys Gly Gly Glu Glu
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Ile Arg Ser Asn Val Gly Glu
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic

<400> SEQUENCE: 105

Asn Val Leu Asp Gly Leu
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic

<400> SEQUENCE: 106

Met Thr Leu Asn Gly Asp Glu
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic

<400> SEQUENCE: 107

Ile Arg Ser Asn Val Gly Glu
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic

<400> SEQUENCE: 108

Leu Val Lys Ser Gly Glu Val
1               5
```

```
<210> SEQ ID NO 109
<211> LENGTH: 7
<212> TYPE: PRT
<213> ORGANISM: Artificial Sequence
<220> FEATURE:
<223> OTHER INFORMATION: Synthetic

<400> SEQUENCE: 109

Val Val Thr Gly Gly Glu Val
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic

<400> SEQUENCE: 110

Leu Val Lys Ser Gly Glu Val
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Ile Arg Ser Asn Met Asp Lys
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic

<400> SEQUENCE: 112

Ile Arg Ser Asn Val Gly Glu
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic

<400> SEQUENCE: 113

Ile Gln Ser Ser Gln Arg Glu
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic

<400> SEQUENCE: 114

Asn Ala Leu Asp Gly Leu
1               5

<210> SEQ ID NO 115
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 115

Thr Tyr Ser Ser Gly Asn
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic

<400> SEQUENCE: 116

Val Val Thr Gly Gly Glu Val
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic

<400> SEQUENCE: 117

Val Tyr Ser Ser Gly Asn
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

Ile Gln Ser Ser Gln Arg Glu
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

Tyr Phe Ser Gly Asp Thr Leu Val
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic

<400> SEQUENCE: 120

Ile Arg Ser Asn Val Gly Glu
1               5

<210> SEQ ID NO 121
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 121

Ala Gly Asp Gly Ser Gly Asn Thr Gly Lys Leu Ile
1               5                   10

<210> SEQ ID NO 122
<211> LENGTH: 17
<212> TYPE: PRT
<213> ORGANISM: Artificial Sequence
<220> FEATURE:
<223> OTHER INFORMATION: Synthetic

<400> SEQUENCE: 122

Ala Gly Ala Gly Gly Phe Leu Asn Ser Gly Gly Ser Lys Tyr Lys Leu
1               5                   10                  15

Thr

<210> SEQ ID NO 123
<211> LENGTH: 11
<212> TYPE: PRT
<213> ORGANISM: Artificial Sequence
<220> FEATURE:
<223> OTHER INFORMATION: Synthetic

<400> SEQUENCE: 123

Ala Phe Met Lys Gly Ser Asn Tyr Lys Leu Thr
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

Ala Thr His Ser Gly Ala Gly Ser Tyr Gln Leu Thr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic

<400> SEQUENCE: 125

Ala Gly Asn Val Gly Gly Thr Gly Lys Leu Ile
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic

<400> SEQUENCE: 126

Gln Arg Arg Asp Thr Gly Asn Gln Phe Tyr
1               5                   10

<210> SEQ ID NO 127
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 127

Ala Leu Ser Glu Ile Lys Asn Gln Gly Gly Lys Leu Ile
1               5                   10

<210> SEQ ID NO 128
<211> LENGTH: 8
<212> TYPE: PRT
<213> ORGANISM: Artificial Sequence
<220> FEATURE:
<223> OTHER INFORMATION: Synthetic

<400> SEQUENCE: 128

Ala Val Arg Pro Gly Glu Leu Ser
1               5

<210> SEQ ID NO 129
<211> LENGTH: 13
<212> TYPE: PRT
<213> ORGANISM: Artificial Sequence
<220> FEATURE:
<223> OTHER INFORMATION: Synthetic

<400> SEQUENCE: 129

Ala Val Arg Asp Glu Gly Gly Ala Thr Asn Lys Leu Ile
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Synthetic

<400> SEQUENCE: 130

Ala Val Asn Ala Gly Gly Gly Ser Gln Gly Asn Leu Ile
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic

<400> SEQUENCE: 131

Ala Val Ser Gly Ser Gly Asp Lys Leu Ile
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Synthetic

<400> SEQUENCE: 132

Ala Ser Phe Ser Gly Gly Tyr Gln Lys Val Thr
1               5                   10

<210> SEQ ID NO 133
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 133

Gly Ala Gly Arg Pro Asn Ser Gly Gly Ser Asn Tyr Lys Leu Thr
1               5                   10                  15

<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

Ala Ala Gly Gly Arg Asp Asp Lys Ile Ile
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Synthetic

<400> SEQUENCE: 135

Ala Val Arg Pro Ser Asn Gln Ala Gly Thr Ala Leu Ile
1               5                   10

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Ala Ser Leu Tyr Phe Asn Lys Phe Tyr
1               5

<210> SEQ ID NO 137
<211> LENGTH: 4
<212> TYPE: PRT
<213> ORGANISM: Artificial Sequence
<220> FEATURE:
<223> OTHER INFORMATION: Synthetic

<400> SEQUENCE: 137

Ala Ala Ile Gly
1

<210> SEQ ID NO 138
<211> LENGTH: 11
<212> TYPE: PRT
<213> ORGANISM: Artificial Sequence
<220> FEATURE:
<223> OTHER INFORMATION: Synthetic

<400> SEQUENCE: 138

Ala Gly Ala Pro Ser Asn Asp Tyr Lys Leu Ser
1               5                   10

<210> SEQ ID NO 139
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 139

Ala Gly Ala Asp Asn Asn Asp Met Arg
1               5

<210> SEQ ID NO 140
<211> LENGTH: 11
<212> TYPE: PRT
<213> ORGANISM: Artificial Sequence
<220> FEATURE:
<223> OTHER INFORMATION: Synthetic

<400> SEQUENCE: 140

Gly Thr Ser Asn Phe Gly Asn Glu Lys Leu Thr
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Synthetic

<400> SEQUENCE: 141

Ala Glu Asn Asp Ser Gly Gly Gly Ala Asp Gly Leu Thr
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic

<400> SEQUENCE: 142

Ala Ala Met Arg Gly Gly Ala Asp Gly Leu Thr
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic

<400> SEQUENCE: 143

Ala Val Thr Gly Gly Ala Asp Gly Leu Thr
1               5                   10

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Ala Asp Gln Gly Gly Lys Leu Ile
1               5

<210> SEQ ID NO 145
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 145

Ala Met Lys Thr Ser Tyr Asp Lys Val Ile
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Synthetic

<400> SEQUENCE: 146

Ala Ala Ser Gly Gly Ser Asn Tyr Lys Leu Thr
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Synthetic

<400> SEQUENCE: 147

Ala Val Asn Pro Ser Arg Gly Tyr Ser Thr Leu Thr
1               5                   10

<210> SEQ ID NO 148
<211> LENGTH: 9
<212> TYPE: PRT
<213> ORGANISM: Artificial Sequence
<220> FEATURE:
<223> OTHER INFORMATION: Synthetic

<400> SEQUENCE: 148

Ala Val Tyr Gly Asn Asn Arg Leu Ala
1               5

<210> SEQ ID NO 149
<211> LENGTH: 10
<212> TYPE: PRT
<213> ORGANISM: Artificial Sequence
<220> FEATURE:
<223> OTHER INFORMATION: Synthetic

<400> SEQUENCE: 149

Ala Val Gly Tyr Gly Asn Asn Arg Leu Ala
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Synthetic

<400> SEQUENCE: 150

Ala Ala Gly Pro Ser Asn Thr Gly Asn Gln Phe Tyr
1               5                   10

<210> SEQ ID NO 151
<211> LENGTH: 5
<212> TYPE: PRT
<213> ORGANISM: Artificial Sequence
<220> FEATURE:
```

<223> OTHER INFORMATION: Synthetic

<400> SEQUENCE: 151

Ser Glu His Asn Arg
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic

<400> SEQUENCE: 152

Leu Asn His Asp Ala
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic

<400> SEQUENCE: 153

Ser Glu His Asn Arg
1               5

<210> SEQ ID NO 154
<211> LENGTH: 5
<212> TYPE: PRT
<213> ORGANISM: Artificial Sequence
<220> FEATURE:
<223> OTHER INFORMATION: Synthetic

<400> SEQUENCE: 154

Ser Glu His Asn Arg
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic

<400> SEQUENCE: 155

Asp Phe Gln Ala Thr Thr
1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic

<400> SEQUENCE: 156

Ser Gly His Lys Ser
1               5

<210> SEQ ID NO 157
<211> LENGTH: 5
<212> TYPE: PRT
<213> ORGANISM: Artificial Sequence
<220> FEATURE:
<223> OTHER INFORMATION: Synthetic

<400> SEQUENCE: 157

Met Gly His Arg Ala
1               5

<210> SEQ ID NO 158
<211> LENGTH: 5
<212> TYPE: PRT
<213> ORGANISM: Artificial Sequence
<220> FEATURE:
<223> OTHER INFORMATION: Synthetic

<400> SEQUENCE: 158

Met Asn His Glu Tyr
1               5

<210> SEQ ID NO 159
<211> LENGTH: 5
<212> TYPE: PRT
<213> ORGANISM: Artificial Sequence
<220> FEATURE:
<223> OTHER INFORMATION: Synthetic

<400> SEQUENCE: 159

Leu Asn His Asp Ala
1               5

<210> SEQ ID NO 160
<211> LENGTH: 5
<212> TYPE: PRT
<213> ORGANISM: Artificial Sequence
<220> FEATURE:
<223> OTHER INFORMATION: Synthetic

<400> SEQUENCE: 160

Met Gly His Arg Ala
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic

<400> SEQUENCE: 161

Ser Glu His Asn Arg
1               5

<210> SEQ ID NO 162
<211> LENGTH: 5
<212> TYPE: PRT
<213> ORGANISM: Artificial Sequence
<220> FEATURE:
<223> OTHER INFORMATION: Synthetic

<400> SEQUENCE: 162

Met Gly His Arg Ala
1               5

<210> SEQ ID NO 163
<211> LENGTH: 5
<212> TYPE: PRT
<213> ORGANISM: Artificial Sequence
<220> FEATURE:
<223> OTHER INFORMATION: Synthetic

```
<400> SEQUENCE: 163

Leu Gly His Asn Ala
1               5

<210> SEQ ID NO 164
<211> LENGTH: 5
<212> TYPE: PRT
<213> ORGANISM: Artificial Sequence
<220> FEATURE:
<223> OTHER INFORMATION: Synthetic

<400> SEQUENCE: 164

Met Asn His Glu Tyr
1               5

<210> SEQ ID NO 165
<211> LENGTH: 5
<212> TYPE: PRT
<213> ORGANISM: Artificial Sequence
<220> FEATURE:
<223> OTHER INFORMATION: Synthetic

<400> SEQUENCE: 165

Met Gly His Arg Ala
1               5

<210> SEQ ID NO 166
<211> LENGTH: 5
<212> TYPE: PRT
<213> ORGANISM: Artificial Sequence
<220> FEATURE:
<223> OTHER INFORMATION: Synthetic

<400> SEQUENCE: 166

Met Asn His Glu Tyr
1               5

<210> SEQ ID NO 167
<211> LENGTH: 5
<212> TYPE: PRT
<213> ORGANISM: Artificial Sequence
<220> FEATURE:
<223> OTHER INFORMATION: Synthetic

<400> SEQUENCE: 167

Met Asn His Glu Tyr
1               5

<210> SEQ ID NO 168
<211> LENGTH: 6
<212> TYPE: PRT
<213> ORGANISM: Artificial Sequence
<220> FEATURE:
<223> OTHER INFORMATION: Synthetic

<400> SEQUENCE: 168

Asp Phe Gln Ala Thr Thr
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic

<400> SEQUENCE: 169
```

Ser Gly His Thr Ser
1               5

<210> SEQ ID NO 170
<211> LENGTH: 5
<212> TYPE: PRT
<213> ORGANISM: Artificial Sequence
<220> FEATURE:
<223> OTHER INFORMATION: Synthetic

<400> SEQUENCE: 170

Ser Gly His Asp Thr
1               5

<210> SEQ ID NO 171
<211> LENGTH: 5
<212> TYPE: PRT
<213> ORGANISM: Artificial Sequence
<220> FEATURE:
<223> OTHER INFORMATION: Synthetic

<400> SEQUENCE: 171

Ser Gly Asp Leu Ser
1               5

<210> SEQ ID NO 172
<211> LENGTH: 5
<212> TYPE: PRT
<213> ORGANISM: Artificial Sequence
<220> FEATURE:
<223> OTHER INFORMATION: Synthetic

<400> SEQUENCE: 172

Ser Gly His Thr Ala
1               5

<210> SEQ ID NO 173
<211> LENGTH: 5
<212> TYPE: PRT
<213> ORGANISM: Artificial Sequence
<220> FEATURE:
<223> OTHER INFORMATION: Synthetic

<400> SEQUENCE: 173

Met Asn His Glu Tyr
1               5

<210> SEQ ID NO 174
<211> LENGTH: 5
<212> TYPE: PRT
<213> ORGANISM: Artificial Sequence
<220> FEATURE:
<223> OTHER INFORMATION: Synthetic

<400> SEQUENCE: 174

Met Arg His Asn Ala
1               5

<210> SEQ ID NO 175
<211> LENGTH: 5
<212> TYPE: PRT
<213> ORGANISM: Artificial Sequence
<220> FEATURE:
<223> OTHER INFORMATION: Synthetic

<400> SEQUENCE: 175

```
Met Gly His Asp Lys
1               5

<210> SEQ ID NO 176
<211> LENGTH: 5
<212> TYPE: PRT
<213> ORGANISM: Artificial Sequence
<220> FEATURE:
<223> OTHER INFORMATION: Synthetic

<400> SEQUENCE: 176

Met Asp His Glu Asn
1               5

<210> SEQ ID NO 177
<211> LENGTH: 5
<212> TYPE: PRT
<213> ORGANISM: Artificial Sequence
<220> FEATURE:
<223> OTHER INFORMATION: Synthetic

<400> SEQUENCE: 177

Met Asn His Glu Tyr
1               5

<210> SEQ ID NO 178
<211> LENGTH: 5
<212> TYPE: PRT
<213> ORGANISM: Artificial Sequence
<220> FEATURE:
<223> OTHER INFORMATION: Synthetic

<400> SEQUENCE: 178

Lys Gly His Asp Arg
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic

<400> SEQUENCE: 179

Ser Gly His Arg Ser
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic

<400> SEQUENCE: 180

Met Gly His Arg Ala
1               5

<210> SEQ ID NO 181
<211> LENGTH: 6
<212> TYPE: PRT
<213> ORGANISM: Artificial Sequence
<220> FEATURE:
<223> OTHER INFORMATION: Synthetic

<400> SEQUENCE: 181

Phe Gln Asn Glu Ala Gln
```

```
1               5

<210> SEQ ID NO 182
<211> LENGTH: 6
<212> TYPE: PRT
<213> ORGANISM: Artificial Sequence
<220> FEATURE:
<223> OTHER INFORMATION: Synthetic

<400> SEQUENCE: 182

Ser Gln Ile Val Asn Asp
1               5

<210> SEQ ID NO 183
<211> LENGTH: 6
<212> TYPE: PRT
<213> ORGANISM: Artificial Sequence
<220> FEATURE:
<223> OTHER INFORMATION: Synthetic

<400> SEQUENCE: 183

Phe Gln Asn Glu Ala Gln
1               5

<210> SEQ ID NO 184
<211> LENGTH: 6
<212> TYPE: PRT
<213> ORGANISM: Artificial Sequence
<220> FEATURE:
<223> OTHER INFORMATION: Synthetic

<400> SEQUENCE: 184

Phe Gln Asn Glu Ala Gln
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic

<400> SEQUENCE: 185

Ser Asn Glu Gly Ser Lys Ala
1               5

<210> SEQ ID NO 186
<211> LENGTH: 6
<212> TYPE: PRT
<213> ORGANISM: Artificial Sequence
<220> FEATURE:
<223> OTHER INFORMATION: Synthetic

<400> SEQUENCE: 186

Tyr Tyr Glu Lys Glu Glu
1               5

<210> SEQ ID NO 187
<211> LENGTH: 6
<212> TYPE: PRT
<213> ORGANISM: Artificial Sequence
<220> FEATURE:
<223> OTHER INFORMATION: Synthetic

<400> SEQUENCE: 187

Tyr Ser Tyr Glu Lys Leu
1               5
```

```
<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Ser Met Asn Val Glu Val
1               5

<210> SEQ ID NO 189
<211> LENGTH: 6
<212> TYPE: PRT
<213> ORGANISM: Artificial Sequence
<220> FEATURE:
<223> OTHER INFORMATION: Synthetic

<400> SEQUENCE: 189

Ser Gln Ile Val Asn Asp
1               5

<210> SEQ ID NO 190
<211> LENGTH: 6
<212> TYPE: PRT
<213> ORGANISM: Artificial Sequence
<220> FEATURE:
<223> OTHER INFORMATION: Synthetic

<400> SEQUENCE: 190

Tyr Ser Tyr Glu Lys Leu
1               5

<210> SEQ ID NO 191
<211> LENGTH: 6
<212> TYPE: PRT
<213> ORGANISM: Artificial Sequence
<220> FEATURE:
<223> OTHER INFORMATION: Synthetic

<400> SEQUENCE: 191

Phe Gln Asn Glu Ala Gln
1               5

<210> SEQ ID NO 192
<211> LENGTH: 6
<212> TYPE: PRT
<213> ORGANISM: Artificial Sequence
<220> FEATURE:
<223> OTHER INFORMATION: Synthetic

<400> SEQUENCE: 192

Tyr Ser Tyr Glu Lys Leu
1               5

<210> SEQ ID NO 193
<211> LENGTH: 6
<212> TYPE: PRT
<213> ORGANISM: Artificial Sequence
<220> FEATURE:
<223> OTHER INFORMATION: Synthetic

<400> SEQUENCE: 193

Tyr Ser Leu Glu Glu Arg
1               5
```

```
<210> SEQ ID NO 194
<211> LENGTH: 6
<212> TYPE: PRT
<213> ORGANISM: Artificial Sequence
<220> FEATURE:
<223> OTHER INFORMATION: Synthetic

<400> SEQUENCE: 194

Ser Met Asn Val Glu Val
1               5

<210> SEQ ID NO 195
<211> LENGTH: 6
<212> TYPE: PRT
<213> ORGANISM: Artificial Sequence
<220> FEATURE:
<223> OTHER INFORMATION: Synthetic

<400> SEQUENCE: 195

Tyr Ser Tyr Glu Lys Leu
1               5

<210> SEQ ID NO 196
<211> LENGTH: 6
<212> TYPE: PRT
<213> ORGANISM: Artificial Sequence
<220> FEATURE:
<223> OTHER INFORMATION: Synthetic

<400> SEQUENCE: 196

Ser Met Asn Val Glu Val
1               5

<210> SEQ ID NO 197
<211> LENGTH: 6
<212> TYPE: PRT
<213> ORGANISM: Artificial Sequence
<220> FEATURE:
<223> OTHER INFORMATION: Synthetic

<400> SEQUENCE: 197

Ser Val Gly Glu Gly Thr
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Ser Asn Glu Gly Ser Lys Ala
1               5

<210> SEQ ID NO 199
<211> LENGTH: 6
<212> TYPE: PRT
<213> ORGANISM: Artificial Sequence
<220> FEATURE:
<223> OTHER INFORMATION: Synthetic

<400> SEQUENCE: 199

Tyr Asp Glu Gly Glu Glu
1               5
```

```
<210> SEQ ID NO 200
<211> LENGTH: 6
<212> TYPE: PRT
<213> ORGANISM: Artificial Sequence
<220> FEATURE:
<223> OTHER INFORMATION: Synthetic

<400> SEQUENCE: 200

Tyr Tyr Glu Glu Glu Glu
1               5

<210> SEQ ID NO 201
<211> LENGTH: 6
<212> TYPE: PRT
<213> ORGANISM: Artificial Sequence
<220> FEATURE:
<223> OTHER INFORMATION: Synthetic

<400> SEQUENCE: 201

Tyr Tyr Asn Gly Glu Glu
1               5

<210> SEQ ID NO 202
<211> LENGTH: 6
<212> TYPE: PRT
<213> ORGANISM: Artificial Sequence
<220> FEATURE:
<223> OTHER INFORMATION: Synthetic

<400> SEQUENCE: 202

Tyr Tyr Glu Glu Glu Glu
1               5

<210> SEQ ID NO 203
<211> LENGTH: 6
<212> TYPE: PRT
<213> ORGANISM: Artificial Sequence
<220> FEATURE:
<223> OTHER INFORMATION: Artificial Sequence

<400> SEQUENCE: 203

Ser Val Gly Ala Gly Ile
1               5

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Ser Asn Thr Ala Gly Thr
1               5

<210> SEQ ID NO 205
<211> LENGTH: 6
<212> TYPE: PRT
<213> ORGANISM: Artificial Sequence
<220> FEATURE:
<223> OTHER INFORMATION: Synthetic

<400> SEQUENCE: 205

Ser Tyr Gly Val Asn Ser
1               5

<210> SEQ ID NO 206
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 206

Ser Tyr Asp Val Lys Met
1               5

<210> SEQ ID NO 207
<211> LENGTH: 6
<212> TYPE: PRT
<213> ORGANISM: Artificial Sequence
<220> FEATURE:
<223> OTHER INFORMATION: Synthetic

<400> SEQUENCE: 207

Ser Met Asn Val Glu Val
1               5

<210> SEQ ID NO 208
<211> LENGTH: 6
<212> TYPE: PRT
<213> ORGANISM: Artificial Sequence
<220> FEATURE:
<223> OTHER INFORMATION: Synthetic

<400> SEQUENCE: 208

Ser Phe Asp Val Lys Asp
1               5

<210> SEQ ID NO 209
<211> LENGTH: 6
<212> TYPE: PRT
<213> ORGANISM: Artificial Sequence
<220> FEATURE:
<223> OTHER INFORMATION: Synthetic

<400> SEQUENCE: 209

Tyr Phe Ser Glu Thr Gln
1               5

<210> SEQ ID NO 210
<211> LENGTH: 6
<212> TYPE: PRT
<213> ORGANISM: Artificial Sequence
<220> FEATURE:
<223> OTHER INFORMATION: Synthetic

<400> SEQUENCE: 210

Tyr Ser Tyr Glu Lys Leu
1               5

<210> SEQ ID NO 211
<211> LENGTH: 21
<212> TYPE: PRT
<213> ORGANISM: Artificial Sequence
<220> FEATURE:
<223> OTHER INFORMATION: Synthetic

<400> SEQUENCE: 211

Ala Ser Ser His Asn Gly Leu Gly Gln Gly Glu Asp Leu Leu Ser Gly
1               5                   10                  15

Ala Asn Val Leu Thr
            20
```

<210> SEQ ID NO 212
<211> LENGTH: 11
<212> TYPE: PRT
<213> ORGANISM: Artificial Sequence
<220> FEATURE:
<223> OTHER INFORMATION: Synthetic

<400> SEQUENCE: 212

Ala Ser Ser Ile Pro Gly Gly Tyr Gly Tyr Thr
1               5                   10

<210> SEQ ID NO 213
<211> LENGTH: 15
<212> TYPE: PRT
<213> ORGANISM: Artificial Sequence
<220> FEATURE:
<223> OTHER INFORMATION: Synthetic

<400> SEQUENCE: 213

Ala Ser Ser Pro Val Asn Pro Ala Val Ser Tyr Asn Glu Gln Phe
1               5                   10                  15

<210> SEQ ID NO 214
<211> LENGTH: 11
<212> TYPE: PRT
<213> ORGANISM: Artificial Sequence
<220> FEATURE:
<223> OTHER INFORMATION: Synthetic

<400> SEQUENCE: 214

Ala Ser Ser Ala Pro Gly Tyr Asn Glu Gln Phe
1               5                   10

<210> SEQ ID NO 215
<211> LENGTH: 15
<212> TYPE: PRT
<213> ORGANISM: Artificial Sequence
<220> FEATURE:
<223> OTHER INFORMATION: Synthetic

<400> SEQUENCE: 215

Ser Ala Arg Phe Ile Pro Thr Gly Leu Gly Glu Asn Thr Ile Tyr
1               5                   10                  15

<210> SEQ ID NO 216
<211> LENGTH: 14
<212> TYPE: PRT
<213> ORGANISM: Artificial Sequence
<220> FEATURE:
<223> OTHER INFORMATION: Synthetic

<400> SEQUENCE: 216

Ala Ser Ser Leu Thr Ala Gly Ala Tyr Thr Gly Glu Leu Phe
1               5                   10

<210> SEQ ID NO 217
<211> LENGTH: 16
<212> TYPE: PRT
<213> ORGANISM: Artificial Sequence
<220> FEATURE:
<223> OTHER INFORMATION: Synthetic

<400> SEQUENCE: 217

Ala Ser Ser Gln Gly Val Glu Arg Gln Gly Pro Arg Asn Glu Gln Phe
1               5                   10                  15

```
<210> SEQ ID NO 218
<211> LENGTH: 12
<212> TYPE: PRT
<213> ORGANISM: Artificial Sequence
<220> FEATURE:
<223> OTHER INFORMATION: Synthetic

<400> SEQUENCE: 218

Ala Ser Ser Ser Ser Gly Arg Asn Asn Glu Gln Phe
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic

<400> SEQUENCE: 219

Ala Ser Ser Ile Ala His Gly Asp Glu Gln Tyr
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Synthetic

<400> SEQUENCE: 220

Ala Ser Gln Asp Tyr Leu Asn Ser Tyr Asn Glu Gln Phe
1               5                   10

<210> SEQ ID NO 221
<211> LENGTH: 15
<212> TYPE: PRT
<213> ORGANISM: Artificial Sequence
<220> FEATURE:
<223> OTHER INFORMATION: Synthetic

<400> SEQUENCE: 221

Ala Ser Ser Leu Ala Arg Gln Gly Val Asp Gln Glu Thr Gln Tyr
1               5                   10                  15

<210> SEQ ID NO 222
<211> LENGTH: 14
<212> TYPE: PRT
<213> ORGANISM: Artificial Sequence
<220> FEATURE:
<223> OTHER INFORMATION: Synthetic

<400> SEQUENCE: 222

Ala Ser Ser Gln Asp Lys Tyr Arg Gly Asn Glu Lys Leu Phe
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Synthetic

<400> SEQUENCE: 223

Ala Ser Ser Gln Asp Arg Ala Asp Thr Gln Tyr
1               5                   10

<210> SEQ ID NO 224
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 224

Ala Ser Ser Leu Gly Gly Ser Arg Leu Glu Gln Tyr
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Synthetic

<400> SEQUENCE: 225

Ala Ser Ser Pro Leu Asp Arg Gly Leu Ser Gly Glu Leu Phe
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Synthetic

<400> SEQUENCE: 226

Ala Ser Ser Leu Ser Phe Gly Ser Gly Ala Asn Val Leu Thr
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Synthetic

<400> SEQUENCE: 227

Ala Ser Ser Tyr Thr Ser Asn Thr Gly Glu Leu Phe
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Synthetic

<400> SEQUENCE: 228

Ser Ala Arg Gly Tyr Gly Gln Gly Pro Glu Gln Tyr
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Synthetic

<400> SEQUENCE: 229

Ala Ser Ser Pro Gly Thr Pro Phe Ser Tyr Asn Glu Gln Phe
1               5                   10

<210> SEQ ID NO 230
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 230

Ala Ser Ser Phe Ala Val Tyr Gly Gly Glu Leu Phe
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Synthetic

<400> SEQUENCE: 231

Ala Ser Ser Thr Leu Ala Gly Thr Tyr Asn Glu Gln Phe
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Synthetic

<400> SEQUENCE: 232

Ala Ser Ser Leu Gly Pro Pro Gly Gly Glu Gln Phe
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Synthetic

<400> SEQUENCE: 233

Ala Ser Ser Tyr Ser Asn Ala Gly Glu Leu Phe
1               5                   10

<210> SEQ ID NO 234
<211> LENGTH: 13
<212> TYPE: PRT
<213> ORGANISM: Artificial Sequence
<220> FEATURE:
<223> OTHER INFORMATION: Synthetic

<400> SEQUENCE: 234

Ala Ser Ser Leu Gly Leu Ala Gly Asp Asp Glu Gln Phe
1               5                   10

<210> SEQ ID NO 235
<211> LENGTH: 9
<212> TYPE: PRT
<213> ORGANISM: Artificial Sequence
<220> FEATURE:
<223> OTHER INFORMATION: Synthetic

<400> SEQUENCE: 235

Ala Ser Ser Arg Gly Asp Glu Gln Phe
1               5

<210> SEQ ID NO 236
<211> LENGTH: 13
<212> TYPE: PRT
```

<213> ORGANISM: Artificial Sequence
<220> FEATURE:
<223> OTHER INFORMATION: Synthetic

<400> SEQUENCE: 236

Ala Ser Ile Gly Glu Thr Gly Phe Val Glu Thr Gln Tyr
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Synthetic

<400> SEQUENCE: 237

Ala Ser Ser Glu Thr Gly Ile Arg Asp Gly Tyr Thr
1               5                   10

<210> SEQ ID NO 238
<211> LENGTH: 15
<212> TYPE: PRT
<213> ORGANISM: Artificial Sequence
<220> FEATURE:
<223> OTHER INFORMATION: Synthetic

<400> SEQUENCE: 238

Ala Thr Ser Asp Pro Ser Asp Arg Val Gly Gln Glu Thr Gln Tyr
1               5                   10                  15

<210> SEQ ID NO 239
<211> LENGTH: 11
<212> TYPE: PRT
<213> ORGANISM: Artificial Sequence
<220> FEATURE:
<223> OTHER INFORMATION: Synthetic

<400> SEQUENCE: 239

Ala Ser Ser Leu Glu Gly Ser Arg Glu Gln Tyr
1               5                   10

<210> SEQ ID NO 240
<211> LENGTH: 15
<212> TYPE: PRT
<213> ORGANISM: Artificial Sequence
<220> FEATURE:
<223> OTHER INFORMATION: Synthetic

<400> SEQUENCE: 240

Ala Ser Ser Leu His Ile Ala Gly Gly Ile Ser Asp Thr Gln Tyr
1               5                   10                  15

<210> SEQ ID NO 241
<211> LENGTH: 27
<212> TYPE: PRT
<213> ORGANISM: Artificial Sequence
<220> FEATURE:
<223> OTHER INFORMATION: Synthetic

<400> SEQUENCE: 241

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 242

```
<211> LENGTH: 19
<212> TYPE: PRT
<213> ORGANISM: Artificial Sequence
<220> FEATURE:
<223> OTHER INFORMATION: Synthetic

<400> SEQUENCE: 242

Ala Thr Asn Phe Ser Leu Leu Lys Gln Ala Gly Asp Val Glu Glu Asn
1               5                   10                  15

Pro Gly Pro

<210> SEQ ID NO 243
<211> LENGTH: 141
<212> TYPE: PRT
<213> ORGANISM: Artificial Sequence
<220> FEATURE:
<223> OTHER INFORMATION: Synthetic

<400> SEQUENCE: 243

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 244
<211> LENGTH: 177
<212> TYPE: PRT
<213> ORGANISM: Artificial Sequence
<220> FEATURE:
<223> OTHER INFORMATION: Synthetic

<400> SEQUENCE: 244

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
```

```
                  100                 105                 110
Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 245
<211> LENGTH: 137
<212> TYPE: PRT
<213> ORGANISM: Artificial Sequence
<220> FEATURE:
<223> OTHER INFORMATION: Synthetic

<400> SEQUENCE: 245

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala
        50                  55                  60

Trp Ser Asn Gln Thr Ser Phe Thr Cys Gln Asp Ile Phe Lys Glu Thr
65                  70                  75                  80

Asn Thr Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 246
<211> LENGTH: 173
<212> TYPE: PRT
<213> ORGANISM: Artificial Sequence
<220> FEATURE:
<223> OTHER INFORMATION: Synthetic

<400> SEQUENCE: 246

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Ser Thr Asp Pro Gln Ala Tyr Lys
        50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
```

```
                    85                  90                  95
His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 247
<211> LENGTH: 141
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 247

```
Xaa Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

<210> SEQ ID NO 248
<211> LENGTH: 177
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 248

```
Xaa Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
```

```
                  35                  40                  45
Gly Lys Glu Val His Ser Gly Val Cys Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 249
<211> LENGTH: 9
<212> TYPE: PRT
<213> ORGANISM: Artificial Sequence
<220> FEATURE:
<223> OTHER INFORMATION: Synthetic

<400> SEQUENCE: 249

Lys Val Leu Glu His Val Val Arg Val
 1               5

<210> SEQ ID NO 250
<211> LENGTH: 10
<212> TYPE: PRT
<213> ORGANISM: Artificial Sequence
<220> FEATURE:
<223> OTHER INFORMATION: Synthetic

<400> SEQUENCE: 250

Gly Val Tyr Asp Gly Arg Glu His Thr Val
 1               5                  10

<210> SEQ ID NO 251
<211> LENGTH: 9
<212> TYPE: PRT
<213> ORGANISM: Artificial Sequence
<220> FEATURE:
<223> OTHER INFORMATION: Synthetic

<400> SEQUENCE: 251

Ala Leu Leu Glu Glu Glu Glu Gly Val
 1               5

<210> SEQ ID NO 252
<211> LENGTH: 9
<212> TYPE: PRT
<213> ORGANISM: Artificial Sequence
<220> FEATURE:
<223> OTHER INFORMATION: Synthetic

<400> SEQUENCE: 252

Lys Val Asp Glu Leu Ala His Phe Leu
 1               5
```

```
<210> SEQ ID NO 253
<211> LENGTH: 10
<212> TYPE: PRT
<213> ORGANISM: Artificial Sequence
<220> FEATURE:
<223> OTHER INFORMATION: Synthetic

<400> SEQUENCE: 253

Ala Leu Ala Glu Thr Ser Tyr Val Lys Val
1               5                   10

<210> SEQ ID NO 254
<211> LENGTH: 9
<212> TYPE: PRT
<213> ORGANISM: Artificial Sequence
<220> FEATURE:
<223> OTHER INFORMATION: Synthetic

<400> SEQUENCE: 254

Ala Leu Ser Asn Lys Val Asp Glu Leu
1               5

<210> SEQ ID NO 255
<211> LENGTH: 9
<212> TYPE: PRT
<213> ORGANISM: Artificial Sequence
<220> FEATURE:
<223> OTHER INFORMATION: Synthetic

<400> SEQUENCE: 255

Gly Val Ala Gly Asp Val Ser Ala Val
1               5
```

TCR, POLYPEPTIDE, EXPRESSION VECTOR, HOST CELL, PHARMACEUTICAL COMPOSITION AND METHOD FOR OBTAINING TCR

CROSS REFERENCE TO RELATED APPLICATIONS

The present application claims a priority to China patent application No. 202110258515.1 filed on Mar. 9, 2021, which is incorporated herein by reference in its entirety for all purposes and made a part of this specification.

REFERENCE TO SEQUENCE LISTING

A sequence listing is submitted as an ASCII formatted text filed via EFS-Web, with a file name of "Sequence_listing.TXT", a creation date of May 9, 2022, and a size of 131,519 bytes. The sequence Listing filed via EFS-Web is part of the specification and is incorporated in its entirety by reference herein.

TECHNICAL FIELD

The present application relates to the technical field of cellular immunotherapy, and, in particular, to a T cell receptor capable of recognizing MAGE-A4 antigen peptide, a polypeptide, an expression vector, a host cell, a pharmaceutical composition and a method for obtaining TCR.

BACKGROUND

A melanoma antigen family A4 (MAGE A4) belongs to a cancer-testis antigen family. It is expressed in a variety of tumor cells, but only in normal tissues of adult testis and placenta. Therefore, MAGE A4 is an ideal tumor treatment target. However, because this target is not a tumor cell surface antigen, it is difficult to specifically recognize the target by using an existing antibody technology and chimeric antigen receptor technology.

A T cell receptor (TCR) is an antibody-like molecule expressed on the surface of T cells. It can be divided into αβ-type TCR and γδ-type TCR according to proteins constituting the receptor. Among them, αβ-type TCR can specifically recognize a short antigenic peptide MHC complex presented by a major histocompatibility complex (MHC; a human MHC is called human leucocyte antigen (HLA)). Therefore, TCR can specifically recognize an intracellular cancer antigen presented to a surface of tumor cells by tumor cell MHC, such as MAGE A4, which can break through a limitation present in existing technologies such as the aforementioned antibody technology and chimeric antigen receptor technology.

TCR has diversity, and this diversity is considered to be one of the important mechanisms of host defense. Diversity is produced due to random recombination, insertion, deletion and replacement of different αβ-type TCR gene fragments, which form a polymorphic TCR library. Theoretically, the gene sequence encoding TCR in a genome can create $10^{15}$ to $10^{20}$ TCR clones (one clone is a group of T cells expressing a specific TCR).

At present, in some related technologies, a TCR sequences of a specific target is mainly screened through an in vitro test by those skilled in the art. For example, in some related technologies, TCR sequences of MAGE A4 or MAGE B2 are screened by stimulating naïve T cells in vitro to generate a new TCR sequence. Although the specific TCR-T screened by this method can identify its specific target and pass a functional verification (cell killing, mouse tumor eradicating experiment, or the like), T cells obtained by the above method is not subjected to thymus negative selection to remove their autoimmunity, therefore, TCR-T cells thus constructed may attack one's own normal tissues and produce immunotoxicity. For example, in some related technologies, MAGE-A3 TCR-T cells obtained via in vitro screening abnormally recognize cardiac myonectin since they are not subjected to thymus negative screening, resulting in intolerable cardiotoxicity in clinical trials.

In addition, at present, sarcoma is primarily selected as an indication for clinical development and research in clinical applications in TCR-T technologies for MAGE A4, but this indication accounts for an extremely low proportion in tumor patients in China.

BRIEF SUMMARY

In view of this, the present application provides a natural T cell receptor (TCR) that specifically recognizes MAGE-A4 positive tumors, a TCR expression vector and a host cell, for the treatment of tumor diseases.

In a first aspect, the present application provides a T cell receptor (TCR) that can specifically recognizes MAGE-A4 antigenic peptide, which includes a TCRα Polypeptide having at least 90% identity with any one selected from a group consisting of sequences of SEQ ID No: 1 to SEQ ID No: 30 and a TCRβ polypeptide having at least 90% identity with any one selected from a group consisting of sequences of SEQ ID No: 31 to SEQ ID No: 60, in which the TCRα polypeptides are in one-to-one correspondence with the TCRβ polypeptides in order.

In some embodiments, the antigenic peptide is HLA-A2 restricted. For example, in some further embodiments of the present application, the HLA-A2 is HLA-A*0201 typing.

In some embodiments, sequences of SEQ ID No: 1 to SEQ ID No: 30 sequentially contain a sequence having at least 95% identity with CDRα1 (SEQ ID No: 61 to SEQ ID No: 90), CDRα2 (SEQ ID No: 91 to SEQ ID No: 120) and CDRα3 (SEQ ID No: 121 to SEQ ID No: 150), in which the CDRα1, the CDRα2 and the CDRα3 are in one-to-one correspondence with each other in order; and sequences of SEQ ID No: 31 to SEQ ID No: 60 sequentially contain a sequence having at least 95% identity with CDRβ1 (SEQ ID No: 151 to SEQ ID No: 180), CDRβ2 (SEQ ID No: 181 to SEQ ID No: 210) and CDRβ3 (SEQ ID No: 211 to SEQ ID No: 240), in which the CDRβ1, the CDRβ2 and the CDRβ3 are in one-to-one correspondence with one another in order. For example, TCRα polypeptide of SEQ ID No: 1 contains a sequence having at least 95% identity with CDRα1 of SEQ ID No: 61, a sequence having at least 95% identity with CDRα2 of ID No: 91, and a sequence having at least 95% identity with CDRα3 of SEQ ID No: 121, and so on. For another example, TCRβ polypeptide of SEQ ID No: 31 contains a sequence having at least 95% identity with CDRβ1 of SEQ ID No: 151, a sequence having at least 95% identity with CDRβ2 of SEQ ID No: 181, and a sequence having at least 95% identity with CDRβ3 of SEQ ID No: 211, and so on.

In some further embodiments, the sequences of SEQ ID No: 1 to SEQ ID No: 30 sequentially contain a sequence having at least 99% identity with CDRα1 (SEQ ID No: 61 to SEQ ID No: 90), CDRα2 (SEQ ID No: 91 to SEQ ID No: 120) and CDRα3 (SEQ ID No: 121 to SEQ ID No: 150), in which the CDRα1, the CDRα2 and the CDRα3 are in one-to-one correspondence with each other in order; and the sequences of SEQ ID No: 31 to SEQ ID No: 60 sequentially contain a sequence having at least 95% identity with CDRβ1 (SEQ ID No: 151 to SEQ ID No: 180), CDRβ2 (SEQ ID No: 181 to SEQ ID No: 210) and CDRβ3 (SEQ ID No: 211 to SEQ ID No: 240), in which the CDRβ1, the CDRβ2 and the CDRβ3 are in one-to-one correspondence with each other in order. For example, TCRα polypeptide of SEQ ID No: 1 contains a sequence having at least 99% identity with CDRα1 of SEQ ID No: 61, a sequence having at least 99% identity with CDRα2 of ID No: 91, and a sequence having at least 99% identity with CDRα3 of SEQ ID No: 121, and so on. For another example, TCRβ polypeptide of SEQ ID No: 31 contains a sequence having at least 99% identity with CDRβ1 of SEQ ID No: 151, a sequence having at least 99% identity with CDRβ2 of SEQ ID No: 181, and a sequence having at least 99% identity with CDRβ3 of SEQ ID No: 211, and so on.

In some embodiments, the sequences of SEQ ID No: 1 to SEQ ID No: 30 sequentially contain CDRα1 (SEQ ID No: 61 to SEQ ID No: 90), CDRα2 (SEQ ID No: 91 to SEQ ID No: 120) and CDRα3 (SEQ ID No: 121 to SEQ ID No: 150), in which the CDRα1, the CDRα2 and the CDRα3 are in one-to-one correspondence with each other in order; and the sequences of SEQ ID No: 31 to SEQ ID No: 60 sequentially contain CDRβ1 (SEQ ID No: 151 to SEQ ID No: 180), CDRβ2 (SEQ ID No: 181 to SEQ ID No: 210) and CDRβ3 (SEQ ID No: 211 to SEQ ID No: 240), in which the CDRβ1, the CDRβ2 and the CDRβ3 are in one-to-one correspondence with each other in order. For example, TCRα polypeptide of SEQ ID No: 1 contains CDRα1 of SEQ ID No: 61, CDRα2 of ID No: 91, and CDRα3 of SEQ ID No: 121, and so on. For another example, TCRβ polypeptide of SEQ ID No: 31 contains CDRβ1 of SEQ ID No: 151, CDRβ2 of SEQ ID No: 181, and CDRβ3 of SEQ ID No: 211, and so on.

In some embodiments, the TCRα polypeptide has at least 95% identity with any one selected from a group consisting of sequences of SEQ ID No: 1 to SEQ ID No: 31, and the TCR β polypeptide has at least 95% identity with any one selected from a group consisting of sequences of SEQ ID No: 32 to SEQ ID No: 62, in which all of the TCRα polypeptides are in one-to-one correspondence with all of the TCRβ polypeptides in order.

In the present application, the TCRα polypeptide has at least 99% identity with any one selected from a group consisting of sequences of SEQ ID No: 1 to SEQ ID No: 31, and the TCRβ polypeptide has at least 99% identity with any one selected from a group consisting of sequences of SEQ ID No: 32 to SEQ ID No: 62, in which all of the TCRα polypeptides are in one-to-one correspondence with all of the TCRβ polypeptides in order.

In a second aspect, the present application provides a polypeptide including TCRα polypeptide having sequences CDRα1 (SEQ ID No: 61 to SEQ ID No: 90), CDRα2 (SEQ ID No: 91 to SEQ ID No: 120) and CDRα3 (SEQ ID No: 121 to SEQ ID No: 150) and TCRβ polypeptide having sequences CDRβ1 (SEQ ID No: 151 to SEQ ID No: 180), CDRβ2 (SEQ ID No: 181 to SEQ ID No: 210) and CDRβ3 (SEQ ID No: 211 to SEQ ID No: 240).

In some embodiments, the polypeptide includes a TCRα polypeptide having at least 90% identity with any one selected from a group consisting of amino acid sequences of SEQ ID No: 1 to SEQ ID No: 30 and a TCRβ polypeptide having at least 90% identity with any one selected from a group consisting of amino acid sequences of SEQ ID No: 31 to SEQ ID No: 60.

In some embodiments, the polypeptide includes a TCRα polypeptide having at least 95% identity with any one selected from a group consisting of amino acid sequences of SEQ ID No: 1 to SEQ ID No: 30 and a TCRβ polypeptide having at least 95% identity with any one selected from a group consisting of amino acid sequences of SEQ ID No: 31 to SEQ ID No: 60.

In some embodiments, the polypeptide includes a TCRα polypeptide of any one selected from a group consisting of sequences of SEQ ID No: 1 to SEQ ID No: 30.

In some embodiments, the polypeptide includes a TCRβ polypeptide of any one selected from a group consisting of sequences of SEQ ID No: 31 to SEQ ID No: 60.

In a third aspect, the present application further provides a polynucleotide capable of encoding a polypeptide according to the second aspect.

In a fourth aspect, the present application further provides an expression vector containing the TCR according to the first aspect. In some embodiments, the expression vector is a viral vector. In some embodiments, the expression vector is a retroviral vector or a lentiviral vector.

In some embodiments, the vector further includes a humanized C domain or a murine C domain or a modified humanized C domain. Further, the humanized C domain contains a humanized C subdomain linking an α chain (sequence SEQ ID No: 243) and a humanized C subdomain linking β chain (sequence SEQ ID No: 244); the murine C domain contains a murine C subdomain linking α chain (sequence SEQ ID No: 245) and a murine C subdomain linking β chain (sequence SEQ ID No: 246); and the modified humanized C domain contains a modified humanized C subdomain linking α chain (sequence SEQ ID No: 247) and a modified humanized C subdomain linking α chain (sequence SEQ ID No: 248).

In some embodiments, the expression vector further includes a linker domain, which is located between TCRα polypeptides and TCRβ polypeptides. In some embodiments, the linker domain is selected from a group consisting of sequences of SEQ ID No: 241 or SEQ ID No: 242.

In some embodiments, in the expression vector, a TCRα chain and a TCRβ chain is connected as follow: TCRα chain V(D) j+humanized C subdomain linking α chain (sequence SEQ ID No: 243) or murine C domain linking α chain (sequence SEQ ID No: 245) or modified humanized C subdomain linking α chain (sequence SEQ ID No: 247)+ linker domain (sequence SEQ ID No: 249 or SEQ ID No: 250)+TCRβ chain V(D)J+ humanized C subdomain linking β chain (sequence SEQ ID No: 244) or murine C subdomain linking β chain (sequence SEQ ID No: 246) or modified humanized C subdomain linking β chain (sequence SEQ ID No: 248).

Among them, in a same complete TCR chain, C subdomain linked behind the TCRα chain and C subdomain linked behind the TCRβ chain are of a same source, for example, both are humanized C domain, or both are murine C domain, or both are modified humanized C domain.

In a fifth aspect, the present application further provides a host cell for transforming TCR prepared in the application. In some embodiments, the cells are immune cells.

Further, the immune cells are selected from a group consisting of T cells, NK cells, NKT cells, constant NK cells or other lymphocytes in peripheral blood.

In some embodiments, the host cells are autologous or allogeneic cells isolated from umbilical cord or blood.

In a sixth aspect, the present application further provides a pharmaceutical composition including MAGE-A4 TCR specific cells according to the fifth aspect. In some embodiments, the pharmaceutical composition is used to treat a cancer. In some further embodiments, the cancer is selected from a group consisting of esophageal cancer, gastric cancer, bladder cancer, head and neck tumor or sarcoma.

In a seventh aspect, the present application provides a method for obtaining the TCR according to the first aspect. In some embodiments, the method includes the following steps: (1) Obtaining human MAGE-A4 positive (HLA-A*02:01) tumor tissue by immunohistochemistry and HLA sequence-based typing as potential TCR screening objects, in which the objects are T cells screened by thymus autoimmune tolerance; (2) Preparing a HLA-A*02:01 tetramer containing MAGE-A4 peptide; (3) Digesting the obtained tumor tissue into a single cell suspension, and screening T cells capable of recognizing MAGE-A4 peptide by using HLA-A*02:01 tetramer containing MAGE-A4 peptide prepared in step (2); and (4) Sequencing the T cells screened in step (3) to obtain a TCR V(d)J full-length sequence capable of recognizing MAGE-A4 peptide by single cell multi-omics.

Further, in step (1), the human MAGE-A4 positive (HLA-A*02:01) tumor tissue is obtained by the steps of: obtaining surgical or puncture specimens of a MAGE-A4 positive tumor, cutting sections from the specimens and pasting on slides; baking and dewaxing the slides; performing antigen retrieval on the specimens; performing endogenous peroxidase and nonspecific binding protein blocking, diluting MAGE-A4 primary antibody, incubating at 4° C. overnight, incubating an enzyme-labeled MAGE-A4 secondary antibody, performing diaminobenzidine (DAB) color development, counterstaining with Harris hematoxylin staining solution, sealing with a neutral gum, and scanning; and confirming HLA-A*02:01 typing.

Further, confirming HLA-A*02:01 typing can be performed by two methods:

Method 1: aligning original expression data obtained from single cell sequencing against a reference genome GRCh38 through a count module of CellRanger to generate an aligned bam file "sorted_genome_bam. BAM" and a cell-gene expression matrix; performing single cell HLA typing based on the bam file and a cell barcode file on a software scHLAacount to generate a file containing all HLA typings detected in the samples, a depth statistics file of individual HLA typings, and a cell-HLA typing depth matrix file for confirming the typing of the samples; or Method 2: thawing PBMC samples freeze stored in cell cryopreservation solution, washing the sample twice with PBS, centrifuging to remove the cell cryopreservation solution and obtain cell precipitate, extracting RNA by using Qiagen total RNA extraction kit from the cell precipitate, denaturing the RNA, reversely transcribing the RNA by using Vazyme HiScript to obtain cDNA, perform target enrichment on the cDNA by using Abclonal Gloria HS PCR Kit and primers corresponding to HAL1 and HLA2, respectively, to obtain enriched products, subjecting the enriched products to fragmentation, terminal repair, linker ligation, Index PCR amplification, construction and sequencing, and confirming the typing of the samples.

Further, in step (2), MAGE-A4 HLA-A*02:01 tetramer is prepared by the steps of: selecting an antigen peptide containing MAGE-A4 and combined with HLA-A*02:01; performing peptide exchange; and preparing the tetramer.

Further, performing the peptide exchange includes:
mixing a peptide stock solution with PBS to obtain a diluted peptide solution, and stored on ice;
adding the diluted peptide and peptide Flex-t™ HLA-A*02:01 monomer UVX (280004; Biolegend) into a well plate and mixing;
sealing the well plate with a seal and centrifuging to obtain a supernatant;
removing the seal, placing the well plate on ice and irradiating with a UV lamp; and
sealing the well plate, incubating in the dark to collect a liquid as obtained peptide exchange monomer.

Still further, the tetramer is prepared by the steps of:
transferring the peptide exchange monomer to a micro centrifuge tube or a new plate, adding PE streptavidin, mixing, and incubating in the dark on ice;
adding MD-biotin and $NaN_3$ to PBS to obtain a blocking solution, and adding the blocking solution to the well plate after incubation to stop a reaction;
incubating sealed well plate at 2-8° C. overnight;
preparing a target group:
centrifuging the obtained tetramer and stored on ice in the dark;
adjusting a volume with cell staining buffer and culturing on ice;
washing cells with staining buffer, and culturing the cells in the staining buffer; and
collecting samples by flow cytometry.

Further, step (3) is performed as follows: removing connective tissues attached to a surface the obtained tumor tissue, cutting into pieces, shredding, placing into a centrifuge tube, and adding a digestive solution from Miltenyi gentleMACS discociator KIT to digest the tissues; and inspecting quality of cells by using Bio-Rad TC20 automatic cell counter with a microscope.

Further, in step (4), the T cells screened in step (3) are sequenced by single-cell omics to obtain the T cells TCR V(d)J full-length sequence capable of recognizing MAGE-A4 peptide. In particular, the T cells TCR V(d)J full-length sequence capable of recognizing MAGE-A4 peptide is obtained from a tumor by single-cell immunohistochemical sequencing.

The present application further provides a plasmid virus and cell constructed from TCR-T, including the following steps:
(1) constructing of plasmid;
(2) virus packaging
(3) thawing, stimulating, and activating of PBMC;
(4) lentivirus transducting; and
(5) expanding and culturing of cells.

A use of a composition containing an effective therapeutic dose of MAGE-A4 TCR specific cells for the treatment of a cancer is further provided in the present application.

The present application can achieve at least one of the following beneficial effects.

1. In this application, T cells are obtained from tumor tissues of patients with an esophageal cancer, a bladder cancer or a laryngeal cancer with MAGE A4+ and HLA-A02+, and natural TCRs that can recognize MAGE A4+ are screened therefrom. The TCRs obtained by this method are those subjected to the patient's own thymus negative selection, which excludes the TCRs that can react with normal human tissues, and greatly reduces immunotoxicity due to anti autoantigen from the source.

2. In the present application, the expression amount of MAGE A4 is determined in 20 kinds of cancers by the immunohistochemical method, and the results reveal that the target is highly expressed and positive in esophageal cancer, gastric cancer, bladder cancer and laryngeal cancer of cancer patients in China. Considering that an incidence rate of the above cancers in China is higher than that of sarcomas, TCR sequence targeting esophageal cancer, gastric cancer, bladder cancer, laryngeal cancer and sarcomas, an expression vector, an excipient, cells and preparations containing the TCR sequence, and a clinical application of a product containing the same in cancer patients are developed in the present application.

BRIEF DESCRIPTION OF DRAWINGS

FIG. 1A shows the scanning results of PA001 esophagus moderately differentiated squamous cell carcinoma in clinical phase IA; FIG. 1B shows the scanning results of PA002 esophagus basaloid squamous cell carcinoma with medium to low differentiation in clinical phase IIIB; FIG. 1C shows the scanning results of PA003 glottic moderately differentiated squamous cell carcinoma in clinical phase III; and FIG. 1D shows the scanning results of PA004 bladder invasive urothelial carcinoma in clinical phase II.

FIGS. 6A-6B are pictures showing a therapeutic effect of TCR-T cells screened according to an embodiment on tumor patients, in which FIG. 6A shows a MR result of intravenously infusing TCR01-05 cell preparation ($5e^{10}$ TCR-T cells) on day 0, and FIG. 6B shows a MR result on day 45, that is, 45 days after intravenous infusion.

Figure 1A:
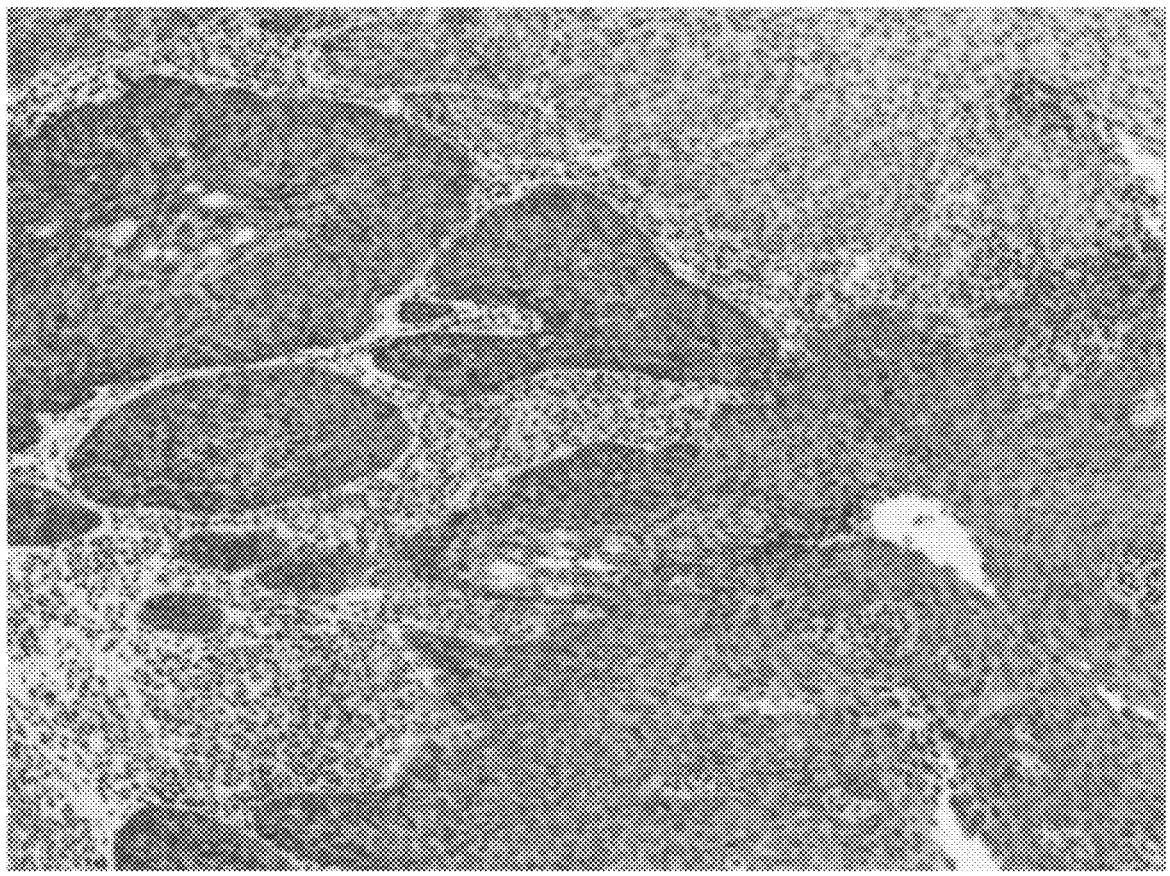
FIGS. 1A to 1D show the scanning and screening results of MAGE-A4 positive tumor sections. Among them.
Figure 1B:
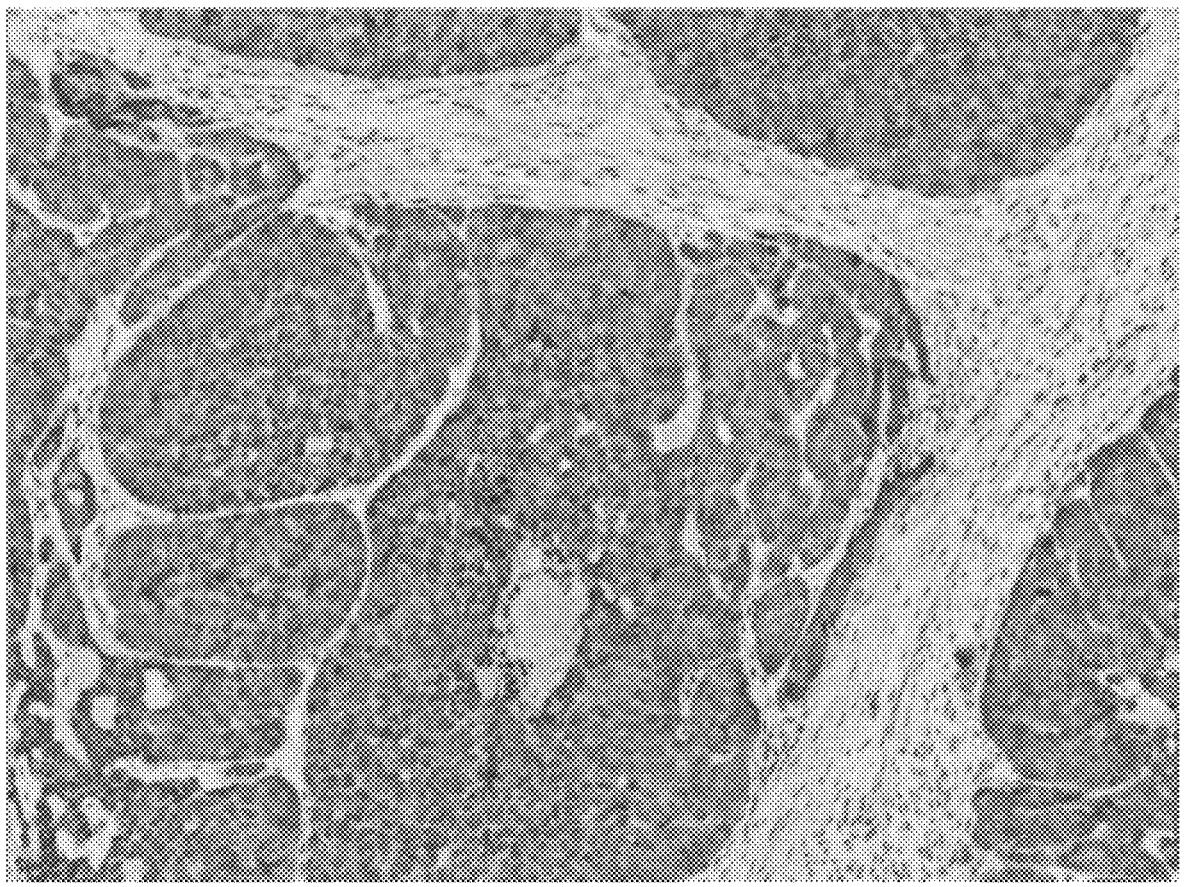
Figure 1C:
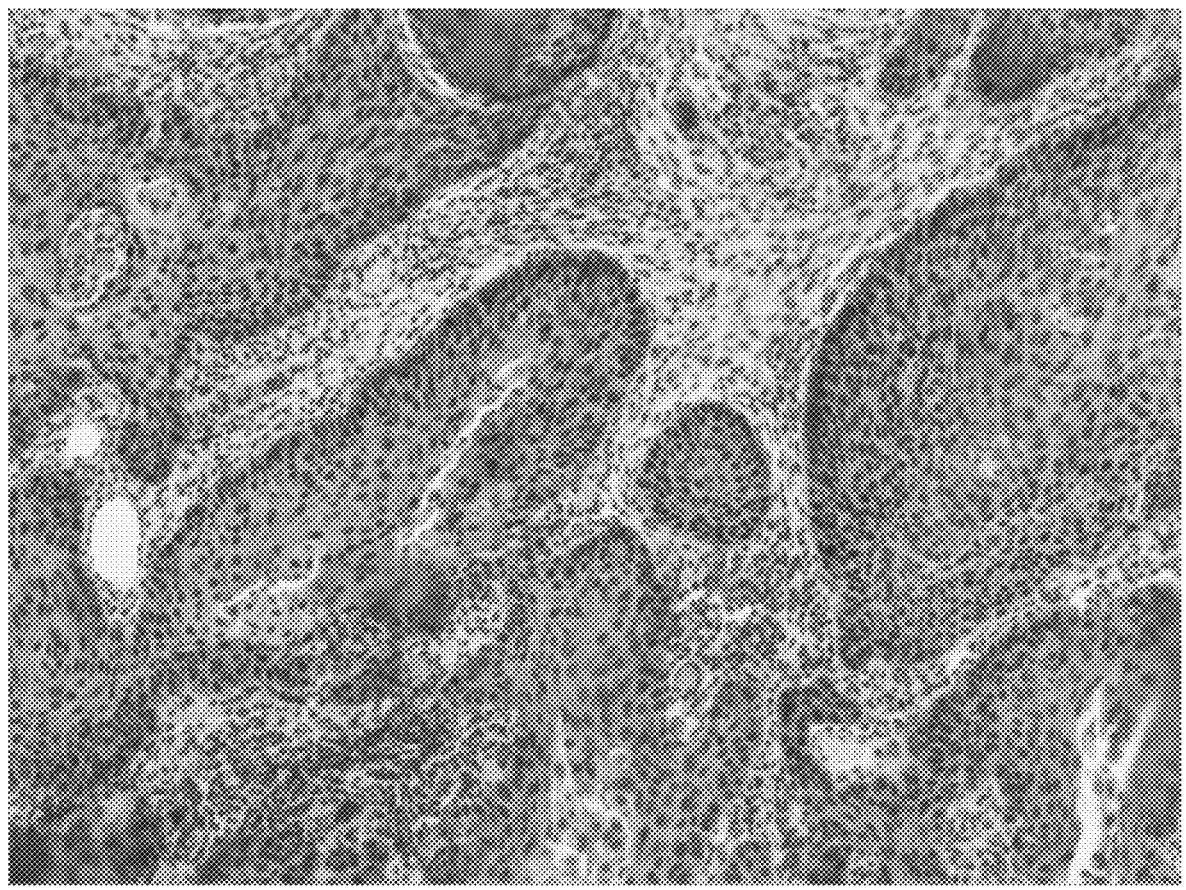
Figure 1D:
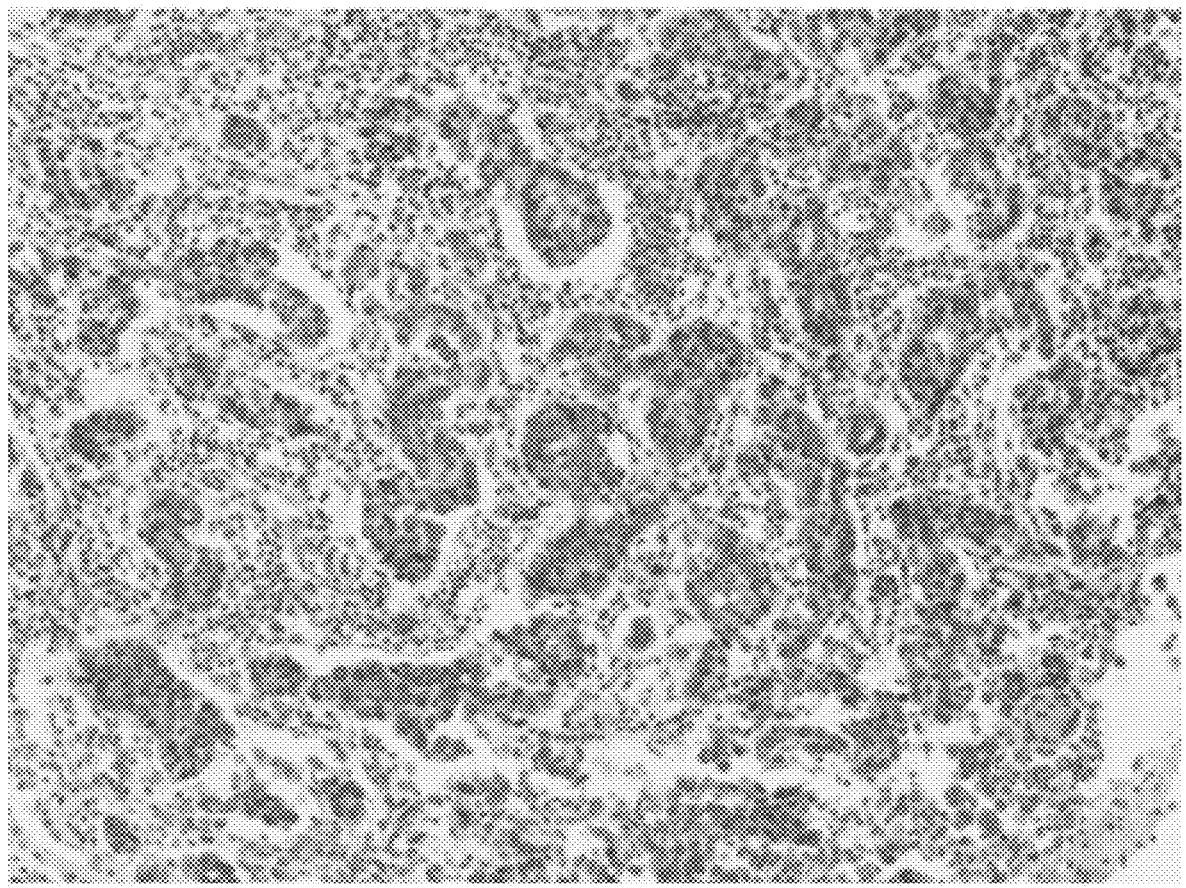

In the Sequence Listing:
SEQ ID NO:1-SEQ ID NO:30: sequences of TCRα polypeptide chain
SEQ ID NO:31-SEQ ID NO:60: sequences of TCRβ polypeptide chain
SEQ ID NO:61-SEQ ID NO90:
SEQ ID NO:91-SEQ ID NO120: sequences of CDRα2 of TCRα polypeptide chain
SEQ ID NO:121-SEQ ID NO:150: sequences of CDRα3 of TCRα polypeptide chain
SEQ ID NO:151-SEQ ID NO:180: sequences of CDRβ1 of TCRβ polypeptide chain
SEQ ID NO:181-SEQ ID NO:210: sequences of CDRβ2 of TCRβ polypeptide chain
SEQ ID NO:211-SEQ ID NO:240: sequences of CDRβ3 of TCRβ polypeptide chain
SEQ ID NO:241-SEQ ID NO:242: Joint domain
SEQ ID NO:243: humanized C domain linking α chain
SEQ ID NO:244: humanized C domain linking β chain
SEQ ID NO:245: murine C domain linking α chain
SEQ ID NO:246: murine C domain linking β chain
SEQ ID NO:247: modified humanized C domain linking α chain
SEQ ID NO:248: modified humanized C domain linking β chain

DETAILED DESCRIPTION

In view of the problems present in existing technologies, the present inventor conducted a lot of research, and found a new technical path, which includes selecting a tumor tissue of a patient with esophageal cancer, bladder cancer or laryngeal cancer showing MAGE A4+ and HLA-A02+, obtaining T cells therefrom, and screening a natural TCR sequence that can recognize MAGE A4+. The TCR obtained by this method is a TCR subjected to the patient's own thymus negative selection, which excludes the TCRs that can react with a normal human tissue, and greatly reduces an off-target toxicity from a source.

In addition, in some related technologies, the TCR-T technology for MAGE A4 primarily selects sarcoma as an indication for clinical development and research in practice, but a proportion of this indication in tumor patients in China is very low. In order to expand the application scope of this technology, the present inventor measured the expression of MAGE A4 in 20 kinds of cancer by immunohistochemical method, and found that the target was highly expressed and positive in esophageal cancer, gastric cancer, bladder cancer and laryngeal cancer of tumor patients in China. Considering that an incidence rate of the above cancers in China is higher than that of sarcomas, a TCR sequence targeting esophageal cancer, gastric cancer, bladder cancer, laryngeal cancer and sarcomas, an expression vector, an excipient, cells and preparations containing the TCR sequence, and a clinical application of a product containing the same in cancer patients are developed in the present application.

The present application is made based on the above discovery.

Unless clearly indicated otherwise in the context, nouns without quantifier modification used in the present application represent one or more, for example, the reference to "cell" includes a plurality of such cells, and the reference to "peptide" includes one or more peptides and their equivalents (for example, polypeptides) known to those skilled in the art.

Example 1

Screening T cells potentially capable of recognizing MAGE-A4 positive solid tumors (HLA-A*02:01 positive patients) by using MAGE-A4 antigen peptide tetramer included the following steps.
(1) Human MAGE-A4 Positive (HLA-A*02:01) Tumor Surgical Specimens or Puncture Tumor Tissues were Obtained by Immunohistochemistry and HLA Sequencing Typing Screening.

In this example, 2 esophageal cancer tissues showing MAGE-A4+, 1 bladder cancer showing MAGE-A4+ and 1 head and neck tumor showing MAGE-A4+ were obtained, and a strong positive expression of MAGE-A4 was confirmed by immunohistochemical method.

The specific methods were as follows:
4 μm-thick sections were cut from a FFPE specimen, attached on glass slides, baked and dewaxed. Antigen repair was performed on these sections.

After blocking endogenous peroxidase and nonspecific binding protein (goat serum blocking solution), MAGE-A4 primary antibody was diluted by a 1:200, and incubated at 4° C. overnight. An enzyme-labeled secondary antibody was incubated for the next day, subjected to DAB color development, counterstained with Harris hematoxylin staining solution, and finally sealed with a neutral gum. Scanning was performed on Vectra3 multispectral scanner under 40×equivalent objective lens. The scanning results are shown in FIGS. 1A-1D. After scanning, the images were analyzed with inForm software to confirm results of screening.

Then HLA-A*02:01 typing was confirmed. In particular, the HLA-A*02:01 typing was confirmed as follows.

Original expression data obtained by single cell sequencing was aligned to a reference genome GRCh38 via a count module of CellRanger (v6.0.2) to generate a BAM file "sorted_genome_bam. BAM" and a cell-gene expression matrix.

Based on the BAM file and a cell barcode file generated by alignment, a software scHLAcount was used to perform HLA typing of single cells, which generated a file of all HLA typing types detected in the sample (labels. tsv), a depth statistics file of individual HLA typing of the specimens (summary.tsv), and a depth matrix file of cell-HLA typing (count_matrix. MTX), for confirming the typing of the specimens.

The HLA typing of 4 patients measured in this Example is shown in Table 1-Table 4.

TABLE 1

| PA001 HLA Type | Read_counts | HLA_cell_number | Total_cell_num | Pos_Cell_ratio |
|---|---|---|---|---|
| A*02:01:176 | 123094 | 11594 | 12342 | 0.9394 |
| B*38:01:01:06 | 116695 | 11248 | 12342 | 0.9114 |
| C* 12:227 | 107872 | 11254 | 12342 | 0.9118 |
| DPA1*01:03:01:34 | 56519 | 7251 | 12342 | 0.5875 |
| DPA11*02:02:08 | 30281 | 5544 | 12342 | 0.4492 |
| DPB1*02:01:19:01 | 23787 | 5365 | 12342 | 0.4347 |
| DPB1*05:01:01:14 | 27268 | 5804 | 12342 | 0.4703 |
| DQA1*03:02:01:02 | 28750 | 5348 | 12342 | 0.4333 |
| DQB1*03:19:01:01 | 31422 | 5475 | 12342 | 0.4436 |
| DRB1*09:01:02:07 | 168840 | 9347 | 12342 | 0.7573 |

TABLE 2

| PA002 HLA Type | Read_counts | HLA_cell_number | Total_cell_num | Pos_Cell_ratio |
|---|---|---|---|---|
| A*02:01:175 | 175081 | 9859 | 10452 | 0.9433 |
| B*54:01:09 | 69756 | 9170 | 10452 | 0.8773 |
| C*01:03:01 | 81025 | 9388 | 10452 | 0.8982 |
| DPA1*04:01:01:02 | 53980 | 5697 | 10452 | 0.5451 |
| DPB1*19:01:01:03 | 38738 | 5669 | 10452 | 0.5424 |
| DQA1*01:03:01:09 | 33252 | 4424 | 10452 | 0.4233 |
| DQB1*04:01:01:02 | 18702 | 4677 | 10452 | 0.4475 |
| DRB1*08:03:02:01 | 82962 | 6894 | 10452 | 0.6596 |

TABLE 3

| PA003 HLA Type | Read_counts | HLA_cell_number | Total_cell_num | Pos_Cell_ratio |
|---|---|---|---|---|
| A*02:01:176 | 84405 | 5362 | 5886 | 0.911 |
| B*08:18 | 84061 | 5065 | 5886 | 0.8605 |
| C*01:17 | 57872 | 5181 | 5886 | 0.8802 |
| DPA1*01:03:01:34 | 40401 | 3787 | 5886 | 0.6434 |
| DPB1*05:01:01:14 | 12676 | 2536 | 5886 | 0.4309 |
| DPB1*124:01:02:01 | 14969 | 2441 | 5886 | 0.4147 |
| DQA1*03:02:01:02 | 12375 | 2092 | 5886 | 0.3554 |
| DQB1*03:03:02:04 | 6243 | 1529 | 5886 | 0.2598 |
| DRB1*09:01:02:07 | 52190 | 4147 | 5886 | 0.7046 |

TABLE 4

| PA004 HLA Type | Read_counts | HLA_cell_number | Total_cell_num | Pos_Cell_ratio |
|---|---|---|---|---|
| A*02:01:175 | 28510 | 2703 | 2983 | 0.9061 |
| B*08:18 | 31832 | 2671 | 2983 | 0.8954 |
| C*03:47 | 2300 | 1287 | 2983 | 0.4314 |
| C*07:429 | 10576 | 2289 | 2983 | 0.7673 |
| DPA1*01:03:17 | 955 | 531 | 2983 | 0.178 |
| DPA1*02:06 | 20972 | 1499 | 2983 | 0.5025 |
| DPB1*22:01:01:01 | 6010 | 918 | 2983 | 0.3077 |
| DPB1*105:01:01:10 | 6470 | 980 | 2983 | 0.3285 |
| DQA1*03:02:01:02 | 18009 | 1350 | 2983 | 0.4526 |
| DQB1*03:01:01:35 | 10154 | 1177 | 2983 | 0.3946 |
| DRB1*09:01:02:07 | 50977 | 1964 | 2983 | 0.6584 |

(2) Preparation of Tetramer Containing MAGE-A4 Peptide HLA-A*02:01

Step S1. 10 mM MAGE-A4 Peptide Stock Solution was Selected, which has the Following Amino Acid Sequence:

1)
KVLEHVVRV; (SEQ ID No: 249)

2)
GVYDGREHTV; (SEQ ID No: 250)

3)
ALLEEEEGV; (SEQ ID No: 251)

4)
KVDELAHFL; (SEQ ID No: 252)

5)
ALAETSYVKV; (SEQ ID No: 253)
and

6)
ALSNKVDEL. (SEQ ID No: 254)

HLA-A*02:01 with an amino acid sequence of GVAGDVSAV (SEQ ID No:255, non naturally present) was selected as a negative control.

S2. Peptide Exchange

S2-1. 5 μl peptide stock solution was mixed with 120 μl PBS buffer to dilute the 10 mM peptide stock solution to 400 μM to obtain a diluted peptide which was stored on ice;

S2-2. 20 μl of diluted peptide prepared in step s2-1 and 20 μl of peptide Flex-t™ HLA-A *02:01 monomer UVX (200 μG/ml) were injected into a 96-well V-shaped plate and mixed by using a pipette;

S2-3. the plate was sealed, and centrifuged at 2500×g at 4° C. for 2 min to obtain a supernatant;

S2-4. the plate was unsealed, placed on the ice and irradiated with an ultraviolet lamp for 30 min, with a distance between the ultraviolet lamp and the plate of 4 cm; and S2-5. the plate was sealed again, and cultured in the dark at 37° C. for 30 min to collect a liquid, which is s peptide exchange monomer.

In order to evaluate the efficiency of peptide exchange, a protocol of HLA class I ELISA was followed.

S3. Preparation of Tetramer

S3-1. 30 μl of the peptide exchange monomer obtained in step S2 was transferred to 1.5 ml micro centrifuge tube or new plate, then added with 3.3 μl of PE streptavidin (purchased from Biolegend under article No. 405204), mixed with a pipette, and incubated in the dark on ice for 30 min;

S3-2. during incubation in step S3-1, 1.6 μl of 50 mM D-biotin and 6 μl of 10% (w/v) $NaN_3$ were added to 192.4 μl PBS buffer to prepare a blocking solution, 2.4 μl of which was added to the solution incubated in step S3-1 under vortex mixing, and mixed with a pipette to stop the reaction; and S3-3. the micro centrifuge tube or plate was incubated at 5° C. overnight to obtain tetramer.

S4. Preparation of Target Group:

S4-1. before dyeing, the tetramer obtained in step S3 was centrifuged in a micro centrifuge tube or plate under 2500×g at 4° C. for 5 min, and then stored on ice in the dark;

S4-2. $2*10^6$ cells were added to 12*75 mm tube or 96-well U-shaped base plate. The volume was adjusted to 200 μl with cell staining buffer. Each Flex-t™ sample was added with 2 μl tetramer obtained in s4-1, mixed and cultured in the dark on ice for 30 min;

S4-3. the cells were washed with the staining buffer twice and recultured in the staining buffer; and S4-4. positive cell samples were collected by using a flow cytometry within 2 hours.

(3) Digesting of a Patient's Tumor Tissue into a Single Cell Suspension

After removing connective tissues from a surface of a tumor issue, the tumor issue was cut into 1 cm*1 cm tissue pieces, fully shredded with a scissor, placed into a 15 ml centrifuge tube. Each tube was added with 6 ml digestive solution of Miltenyi gentleMACS discociator KIT or a mixed solution of self-developed tissue digestive enzyme to digest the tissue.

Cell quality detection: Bio-Rad TC20 automatic cell counter was used in combination with a microscope to accurately detect the quality of the cell suspension, so as to ensure an experimental cell activity of greater than 70% and a cell diameter of less than 40% μm.

(4) Obtaining of TCR V(d)J Full-Length Sequence Capable of Recognizing MAGE-A4 Peptide The TCR V(d)J full-length sequence capable of recognizing the MAGE-A4 peptide segment was obtained from the above four patients' tumors (2 MAGE-A4 positive esophageal cancer tissues, 1 MAGE-A4 positive bladder cancer tissue, and 1 MAGE-A4 positive head and neck tumor tissue).

A total of 30 TCR V(d)J full-length sequences were obtained, numbered TCR01 to TCR30. Each of the TCR V(d)J full-length sequences contains one TCRα polypeptide and one TCRβ polypeptide, the sequence of which is shown in Table 5.

TABLE 5

| TCR | TCRα polypeptide chain | TCRβ polypeptide chain |
| --- | --- | --- |
| TCR01 | SEQ ID NO:1 | SEQ ID NO:31 |
| TCR02 | SEQ ID NO:2 | SEQ ID NO:32 |
| TCR03 | SEQ ID NO:3 | SEQ ID NO:33 |
| TCR04 | SEQ ID NO:4 | SEQ ID NO:34 |
| TCR05 | SEQ ID NO:5 | SEQ ID NO:35 |
| TCR06 | SEQ ID NO:6 | SEQ ID NO:36 |
| TCR07 | SEQ ID NO:7 | SEQ ID NO:37 |
| TCR08 | SEQ ID NO:8 | SEQ ID NO:38 |
| TCR09 | SEQ ID NO:9 | SEQ ID NO:39 |
| TCR10 | SEQ ID NO:10 | SEQ ID NO:40 |
| TCR11 | SEQ ID NO:11 | SEQ ID NO:41 |
| TCR12 | SEQ ID NO:12 | SEQ ID NO:42 |
| TCR13 | SEQ ID NO:13 | SEQ ID NO:43 |
| TCR14 | SEQ ID NO:14 | SEQ ID NO:44 |
| TCR15 | SEQ ID NO:15 | SEQ ID NO:45 |
| TCR16 | SEQ ID NO:16 | SEQ ID NO:46 |
| TCR17 | SEQ ID NO:17 | SEQ ID NO:47 |
| TCR18 | SEQ ID NO:18 | SEQ ID NO:48 |
| TCR19 | SEQ ID NO:19 | SEQ ID NO:49 |
| TCR20 | SEQ ID NO:20 | SEQ ID NO:50 |
| TCR21 | SEQ ID NO:21 | SEQ ID NO:51 |
| TCR22 | SEQ ID NO:22 | SEQ ID NO:52 |
| TCR23 | SEQ ID NO:23 | SEQ ID NO:53 |
| TCR24 | SEQ ID NO:24 | SEQ ID NO:54 |
| TCR25 | SEQ ID NO:25 | SEQ ID NO:55 |
| TCR26 | SEQ ID NO:26 | SEQ ID NO:56 |
| TCR27 | SEQ ID NO:27 | SEQ ID NO:57 |
| TCR28 | SEQ ID NO:28 | SEQ ID NO:58 |
| TCR29 | SEQ ID NO:29 | SEQ ID NO:59 |
| TCR30 | SEQ ID NO:30 | SEQ ID NO:60 |

Example 2

The difference of this example from Example 1 lies that, a different method for confirming HLA-A*02:01 typing in step (2) is adopted. In particular, the method for confirming HLA-A*02:01 typing in this example was as follows:

The sample was freeze stored as PBMC in cell cryopreservation solution. After thawing, the sample was washed twice with PBS to remove the cell cryopreservation solution, and centrifuged to remove the PBS buffer. RNA was extracted from obtained cell precipitate using Qiagen total RNA extraction kit. The RNA was subjected to denaturation, and reversely transcribed using Vazyme HiScript to obtain cDNA.

The cDNA was target enriched twice using Abclonal Gloria HS PCR Kit and corresponding primers of HAL1 and HLA2. 50 ng of the enriched product was subjected to fragmentation, terminal repair, linker connection and Index PCR amplification to construct a sequencing library using Abclonal FS DNA Lib Prep Kit.

The library was subjected to quality inspection and then sequencing on Illumina Novaseq6000 sequencing platform. A target data volume of each sample was 9G.

Example 3 Construction of Plasmid, Virus and Cells from TCR-T (1) Construction of Plasmid A complete TCR sequence (TRA V(d)J+C domain linking α chain+linker domain+TRB V(d)J+C domain linking β chain) was cloned into a target plasmid of lentivirus system (for example, in PGK), and transfected into *E. coli*. Positive clones with kanamycin resistance were selected for amplification and culture, and plasmid was extracted by using Qiagen Plasma Maxi Kit.

The linker domain was modified P2A (SEQ ID No: 241) or P2A linker sequence (SEQ ID No: 242).

In this example, C domain sequences selected for TCR01-TCR05 were SEQ ID No: 243 and SEQ ID No: 244, and the linker domain was modified P2A (SEQ ID No: 241);

C domain sequences selected for TCR06-TCR10 were SEQ ID No: 245 and SEQ ID No: 246, and the linker domain was modified P2A (SEQ ID No: 241);

C domain sequences selected for TCR11-TCR15 were SEQ ID No: 243 and SEQ ID No: 244, and the linker domain was P2A linker sequence (SEQ ID No: 242);

C domain sequences selected for TCR15-TCR20 were SEQ ID No: 245 and SEQ ID No: 246, and the linker domain was P2A linker sequence (SEQ ID No: 242);

C domain sequences selected for TCR16-TCR20 were SEQ ID No: 247 and SEQ ID No: 248, and the linker domain was modified P2A (SEQ ID No: 241);

C domain sequences selected for TCR21-TCR25 were SEQ ID No: 243 and SEQ ID No: 244, and the linker domain was modified P2A (SEQ ID No: 241); and C domain sequences selected for TCR26-TCR30 were SEQ ID No: 243 and SEQ ID No: 244, and the linker domain was C linker sequence (SEQ ID No: 242).

(2) Virus Packaging 1) 24 h before packaging, $8*10^6$ 293 T cells were spread out in a 10 cm Petri dish, supplemented with 10 ml DMEM medium containing 10% FBS, and then cultured in a 5% $CO_2$ incubator at 37° C.;
2) the cells were observed on the day of packaging, and lentivirus packaging was performed when it was confirmed that the cells reached a confluence of 80% (±2%) and assumed a transparent state;
3) reagents used during packaging were removed and balanced to room temperature;
4) 10 ml of the medium in Petri dish and 9 ml serum-free DMEM medium added along the dish wall were transfer to $CO_2$ incubator for use;
5) 450 μl of Opti-MEM was added to a 1.5 ml centrifuge tube, and then added with 7.5 μg of psPAX2, 5 μg of pMD2. G and 10 μg of target plasmid, and mixed with a pipette;
6) another 1.5 ml centrifuge tube was add with 450 μl of Opti-MEM and 22.5 ul of PEIpro reagent, and mixed with a pipette;
7) a mixture obtained in step 5) with a mixture obtained in step 6) were mixed with a pipette, and incubated at room temperature for 10-15 min;
8) a mixture obtained in step 7) was gently dripped into a 10 cm Petri dish, and then transferred to a $CO_2$ incubator for further culturing;
9) after 6 h, the medium in the 10 cm culture dish obtained in step 8) was removed, 10 ml of DMEM medium containing 10% FBS was added to the dish along the dish wall, and the dish was transferred to $CO_2$ incubator for further culturing;
10) After culturing the medium obtained in step 9) for 48 h, supernatant was collected into a 50 ml centrifuge tube, 10 ml of DMEM medium containing 10% FBS was added along the dish wall, the dish was transferred to $CO_2$ incubator for further culturing, and the supernatant containing virus was stored in a refrigerator at 4° C.;
11) after 72 h, the supernatant stored in step 10) was collected into a 50 ml centrifuge tube, and centrifuged at 500×g and 4° C. for 10 min to remove cell debris;
12) the supernatant obtained upon centrifuging in step 11) was filtered through 0.45 μm filter into a new 50 ml centrifugal tube;
13) the supernatant obtained upon filtering in step 12) was added with a quarter volume of PEG8000 concentration reagent and incubated in a shaking table at 4° C. for more than 3 h;
14) the virus solution incubated in step 12) was centrifuged at 2000×g and 4° C. for 40 min to obtain a precipitate, which was added with PBS precooled at 4° C., and gently mixed with a pipette; and
15) The virus obtained in step 14) is divided an packaged into cryopreservation tubes and stored at −80° C. for use.

The virus obtained in the above steps was subjected to virus titration test as follows:

1) on the day of test, the cell density of Jurkat was adjusted to $3*10^5$ cells/ml, added to a 24-well plate by 1 ml cell suspension/each well, and then cultured in 5% $CO_2$ incubator at 37° C. for use;
2) the virus was gradient diluted according to the ratios listed in Table 6 below, in which an additional group of secondary wells was provided for each group;

TABLE 6

| Diluting ratio | Volume of virus (μL) | Volume of 1640 ) medium (μL) | 10 mg/mL polybrene(μL) |
|---|---|---|---|
| 1:50 | 30 | 468.5 | 1.5 |
| 1:100 | 15 | 483.5 | 1.5 |
| 1:200 | 7.5 | 483.5 | 1.5 |
| 1:400 | 3.75 | 494.75 | 1.5 |

3) the diluted virus solution was added to cells, centrifuged at 800 g and 21° C. for 2 h, and then cultured in 5% $CO_2$ incubator at 37° C.;
4) after 60 h, the cells were subjected to FACS test. Titer was calculated by:

Tu/ml=((number of infected cells)×positive rate×(times of dilution))/infected volume For example, when the positive rate of one well with a dilution ratio of 1:100 is 25%, the titer is $(3*10^5) \times 0.25 \times 100/(1.5\ ml) = 5*106$ TU/ml When calculating the titer, only the wells with a positive rate of less than 40% are considered, for the reason that, when the positive rate is higher than 40%, the possibility of multiple virus particles repeatedly infecting one cell will result in inaccurate titer calculation.

(3) Thawing of PBMC:
1) 30 ml of L500 medium was added into 50 ml centrifuge tube and restored to room temperature for use;
2) frozen PBMC was removed from −80° C. refrigerator, quickly placed into a 37° C. water bath, and quickly shaked until there was no visible ice in the frozen tube;
3) thawed cryopreservation tube was disinfected with 75% alcohol, transferred to a biosafety cabinet, slowly dripped into the thawed L500 medium with a 1 ml pipette, and centrifuged at 400 g and 25° C. for 5 min;
4) supernatant was discarded after centrifugation, the cells were resuspended in 30 ml of pre-heated L500 medium, from which 10 ul of the sample was taken for living cell counting, followed by centrifuging at 25° C. and 400 g for 5 min.

(4) Stimulation and Activation of PBMC
1) based on counting results, cells were resuspended in L500 medium and the density of living cells was adjusted to $1-2e^6$/ml;
2) a suspension obtained in step 1) was added with 300 IU/ml IL-2 and 50 ng/ml CD3 antibody, mixed, and transferred to $CO_2$ incubator where they were stimulated and activated for 60 h.

(5) Lentivirus Transduction
1) activation of PBMC 48 hours after activation was observed, and lentivirus transduction was carried out;
2) virus was added by MOI=2 and cells were transferred into carbon dioxide incubator and cultured for 48 h;
3) the cells were transferred into a 50 ml centrifuge tube from which 10 μl was taken for living cell counting, centrifuged at 25° C. and 400 g for 5 min, and washed;
4) based on the results of counting, the transfected cells were resuspended in L500 medium, the cell concentration was adjusted to $1e^6$/ml, IL-2 was added by 100 IU/ml, and the cells were transferred to $CO_2$ incubator for culturing.

(6) Expanding and Culturing of Cells
1) after lentivirus transduction and solution replacing, cells were observed and counted every day, and controlled to have a number of $1e^6$/ml and IL-2 concentration of 100 IU/ml by supplementing medium; and
2) the cells were harvested on the ninth day of culturing.

Example 4 Cell Line Killing Experiment

Positive: A375, h1755, h1395-(MAGE-A4+, HLA-A02+)
Negative: H1299-(MAGE-A4−, HLA-A02−)

Figure 2:
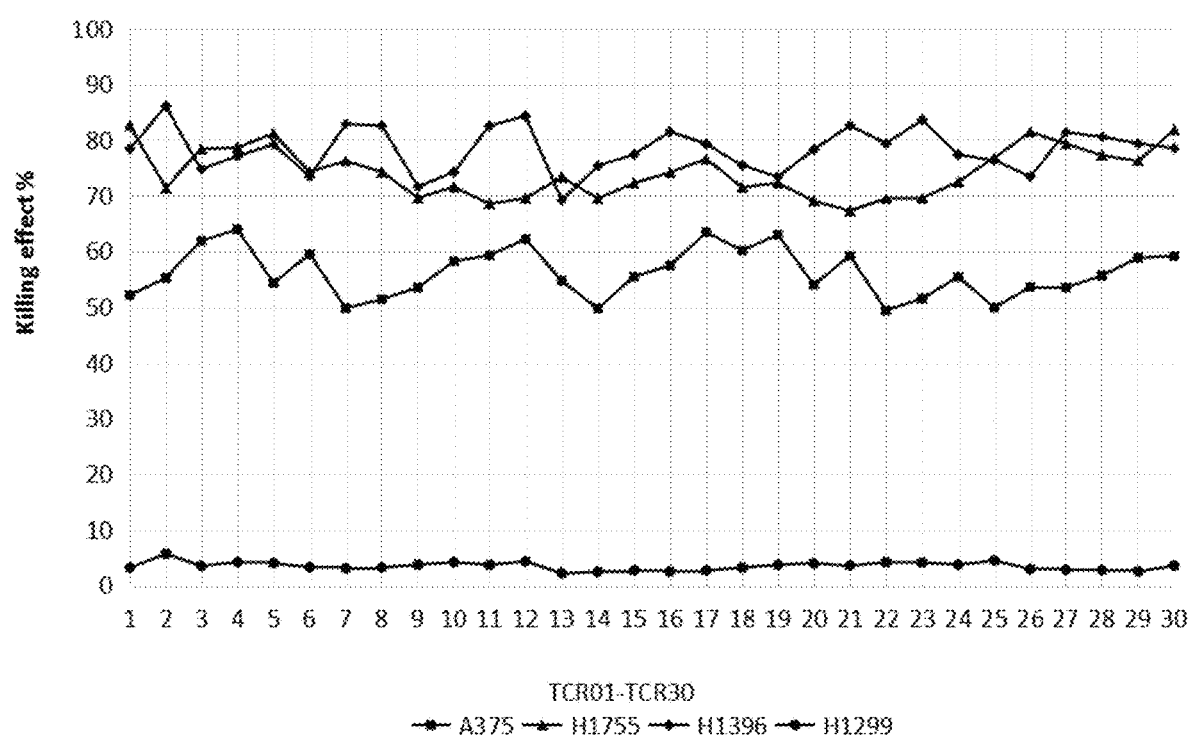
FIG. 2 is a diagram showing a killing effect of a cell line.

T cells screened in this application that can specifically recognize MAGE-A4 positive tumors and target cells, by a ratio of 5:1, were subjected to relevant experiments. The results are shown in FIG. 2, where the abscissa 1-30 represents TCR01-TCR30, respectively, and the ordinate represents a percentage of killing.

The T cells prepared using TCR01-TCR30 were mixed with the target cells with positive A375, H1755 and H1395 respectively by a ratio of T cells to target cells of 5:1. The results are shown in FIG. 2, where the abscissa 1-30 represents TCR01-TCR30, respectively, and the ordinate represents the percentage of killing.

The results show that, TCR-T cells constructed using TCRs screened in this application have the most significant killing effect on target cells with positive H1755 and H1395, with a cell killing percentage of 70%-90%. TCR-T cells constructed using TCRs screened in this application have a relatively significant killing effect on cells with positive A375, with a cell killing percentage of 50%-70%. The killing effect of T cells screened in this application on cells with H1299 showing HLA-A*02:01 negative and having MAGE-A4 knockout is very low, that is, less than 10%.

Example 5 Tumor Clearance Experiment in Mice

NCG mice were inoculated with $1e^7$ A375, H1395, H1755 and H1395 (MAGE-A4−), in which the first three cell lines were natural HLA-A*02:01 and MAGE-A4 positive, and H1395 (MAGE-A4−) has MAGE-A4 knocking-out. When the tumor grew to a volume of 100 $mm^3$, the mice were infused with 200 μl suspension containing $3*10^6$ TCR-T cells at caudal vein for one time, and then subjected to tumor size measurement and weight detection. FIG. 3A-FIG. 3D show the results of tumor clearance, in which the abscissa represents days from medication and the ordinate represents a change in tumor size with the increase of days from medication.

Figure 3A:
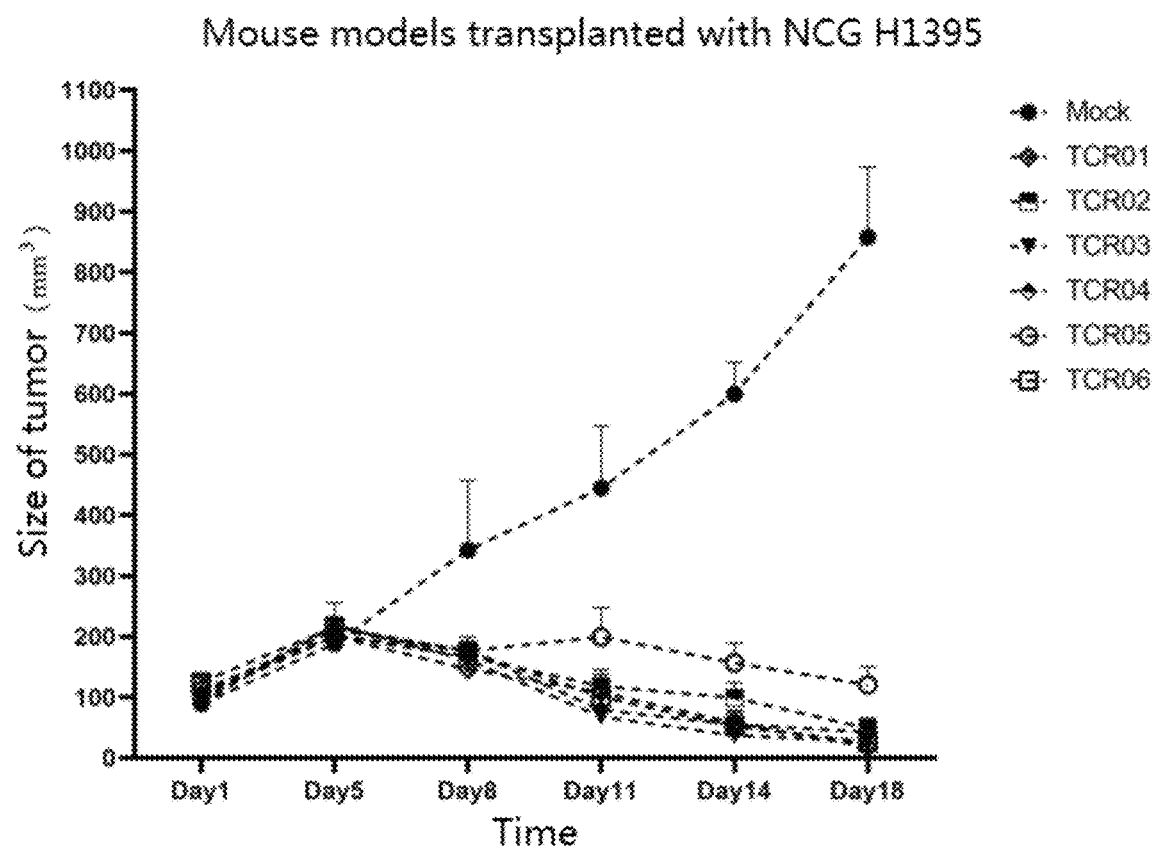
FIGS. 3A to 3D are diagrams showing tumor clearance effect in an experiment.

FIG. 3A shows that, in the NCG H1395 tumor mice having an initial tumor size of about 100 $mm^3$, there is a small increase in 1-5 days after TCR-T injection, that is, the tumor size being increased to 200 $mm^3$; and during 5-18 days, the tumor size is decreased significantly. The tumor size in the control group MOCK is increased to 800 $mm^3$ on the 18th day, decreased to 100 $mm^3$ or below after injection treatment, and after TCR05 injection, remains at about 100 $mm^3$. The tumor size of other cells after TCR-T injection was decreased significantly, approaching 0.

Figure 3B:
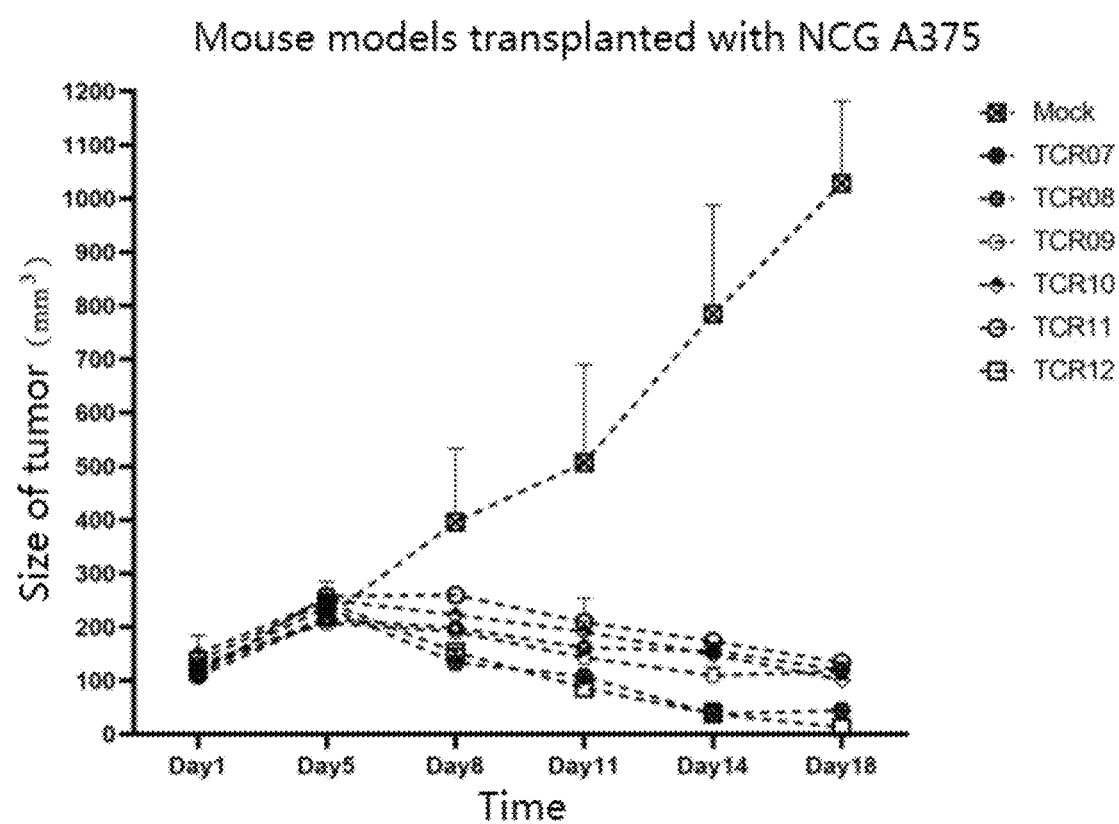

FIG. 3B shows that, in the NCG A375tumor mice having an initial tumor size of about 100 $mm^3$, there is a small increase in 1-8 days after TCR-T injection, that is, the tumor size being increased to 250 $mm^3$; and during 8-18 days, the tumor size is decreased significantly. The tumor size in the control group MOCK is increased to 1000 $mm^3$ or above on the 18th day, and decreased to 100 $mm^3$ or below after injection treatment. The tumor size of other cells after TCR07 and TCR12 injection approached 0, showing a good result.

Figure 3C:
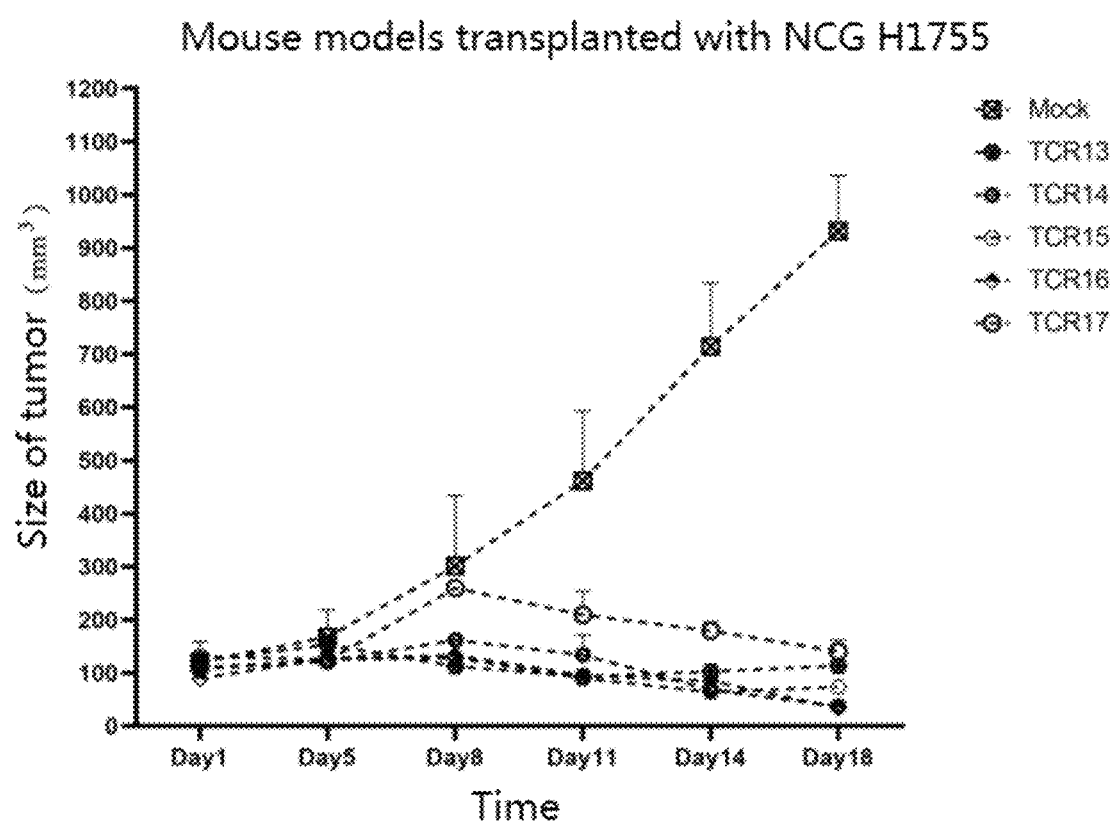

FIG. 3C shows that, in the NCG H1755 tumor mice having an initial tumor size of about 100 mm³, the tumor size in the control group MOCK is increased to 900 mm³ during 1-18 days. In the TCR-T treatment group, the tumor size fluctuates greatly, except for TCR17 group. In other groups, the tumor size fluctuates gently after TCR-T cell injection, and an overall volume of cells is not increased within 18 days and remains at or below 100 mm³.

Figure 3D:
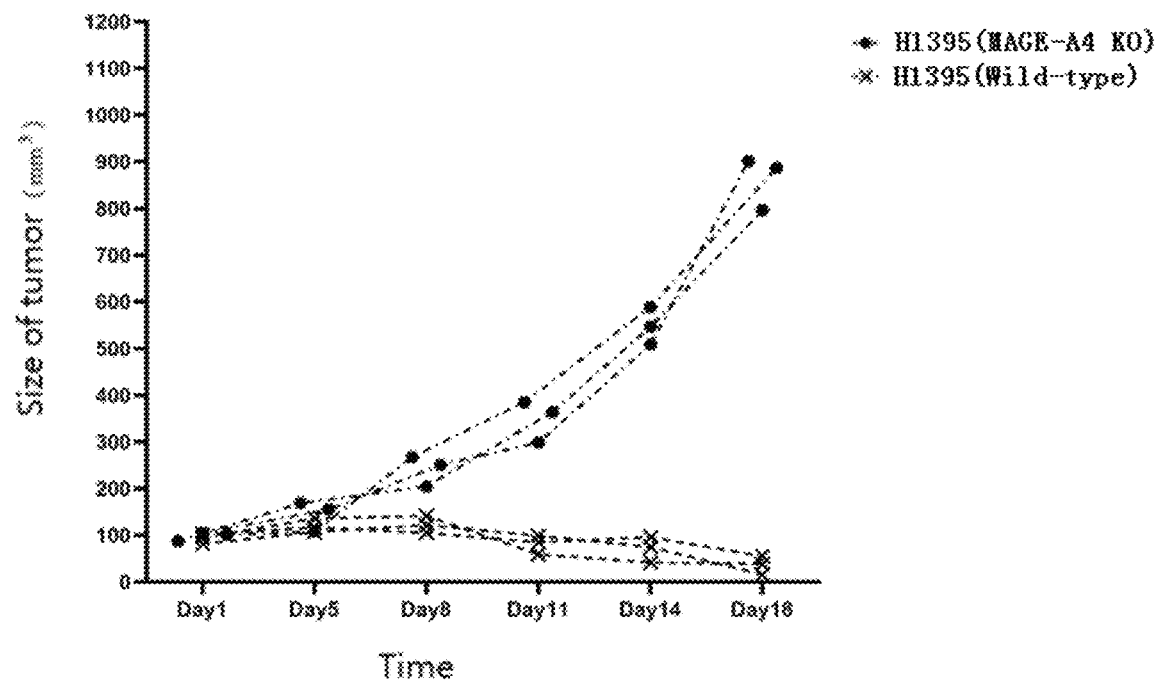

FIG. 3D shows that, in the tumor mice of H1395 (MAGE-A4− and HLA-A02+) with MAGE-A4 knockout or wild-type H1395 (MAGE-A4+ and HLA-A02+) tumor mice having an initial tumor size of about 100 mm³, treatment of TCR01-05-T cells mixture are significantly impaired when the tumor cells assume MAGE-A4 negative, and the tumor size reaches 800-900 mm³ 18 days after injection. When the tumor cells assume MAGE-A4 positive, injection of TCR-T cells according to the present application can significantly inhibit the increase of cell volume, which is controlled to be 100 mm³ or below on the 18$^{th}$ day from injection.

Figure 3E:
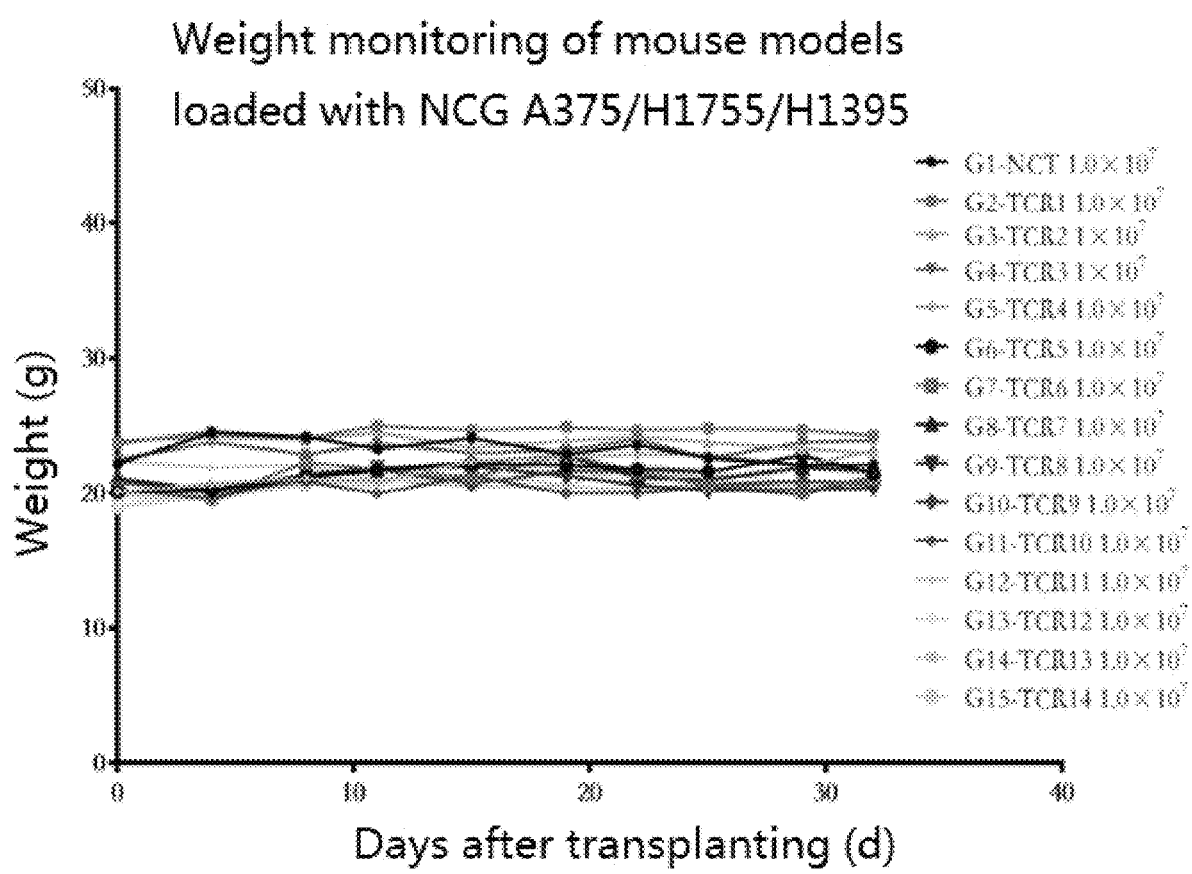
FIG. 3E is a diagram showing the change in weight of experimental mice.

FIG. 3E shows a weight change of mice after injection. It can be seen that, there is no significant change in the weight of mice during the whole injection period, indicating that TCR-T cells according to the present application will not cause obvious toxic reaction after injection.

The results from FIG. 3A to FIG. 3E show that, the constructed TCR-T cells have good tumor inhibition effect and low toxicity in vivo.

Example 6 IFN ELISA Test Confirming No Reaction with Normal Cell Lines

TCR01-TCR15 were selected to react with 11 kinds of normal tissue cells and positive h1755 (MAGE-A4+ and HLA-A02+) cells. INF content in individual cells were detected after 3 days. The selected normal tissue cells are shown in Table 7 below:

TABLE 7

| Chinese name of primary cells | Article No. |
| --- | --- |
| Pulmonary type II alveolar epithelial cells | CTCC-A005-PC |
| Cardiomyocyte | CTCC-C002-PC |
| Esophageal epithelial cells | CTCC-D001-PC |
| Gastric mucosal epithelial cells | CTCC-D004-PC |
| Intestinal mucosal epithelial cells | CTCC-D007-PC |
| Colonic mucosal epithelial cells | CTCC-D011-PC |

TABLE 7-continued

| Chinese name of primary cells | Article No. |
| --- | --- |
| Gallbladder epithelial cells | CTCC-D014-PC |
| Hepatic parenchymal cells | CTCC-D017-PC |
| Renal tubular epithelial cells | CTCC-U002-PC |
| Bladder epithelial cells | CTCC-U008-PC |
| Islet cells | CTCC-G004-PC |

Figure 4A:
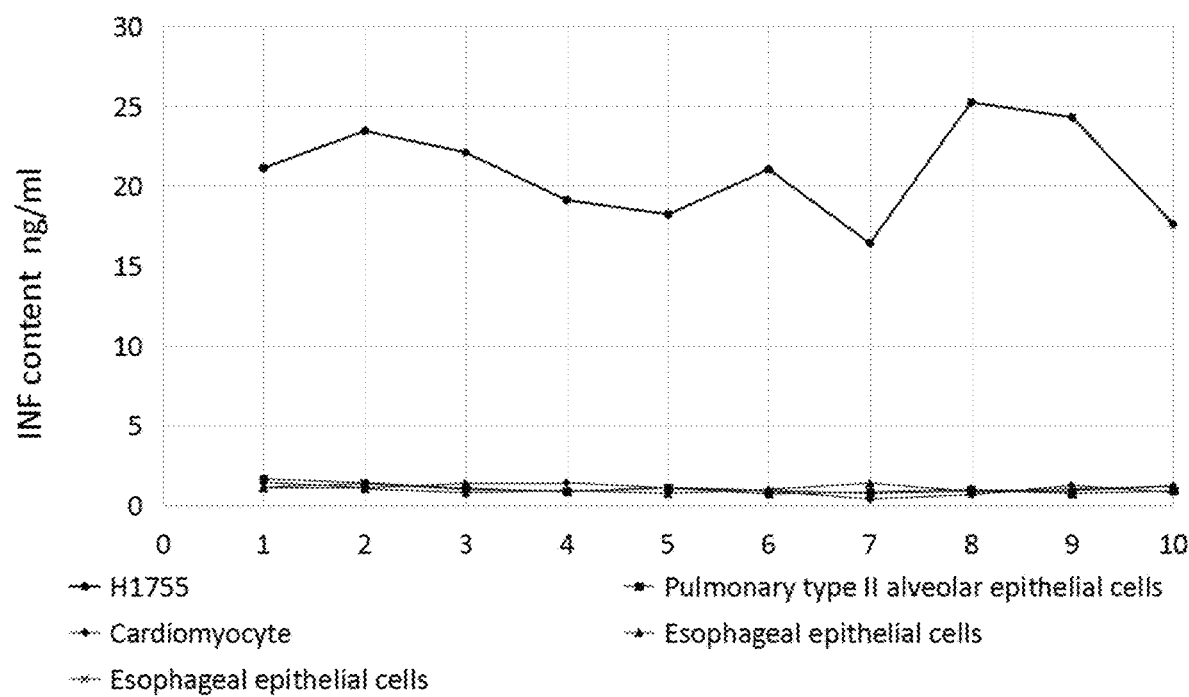
FIGS. 4A to 4C are diagrams show results of IFN ELISA experiments.
Figure 4B:
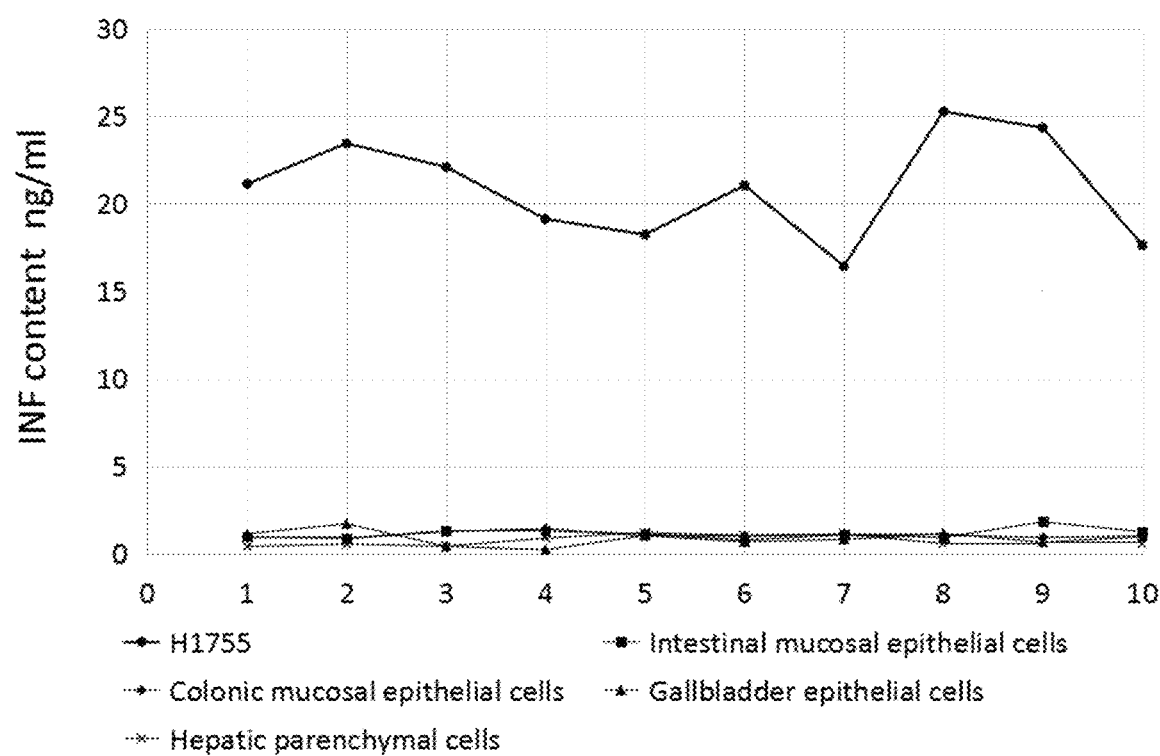
Figure 4C:
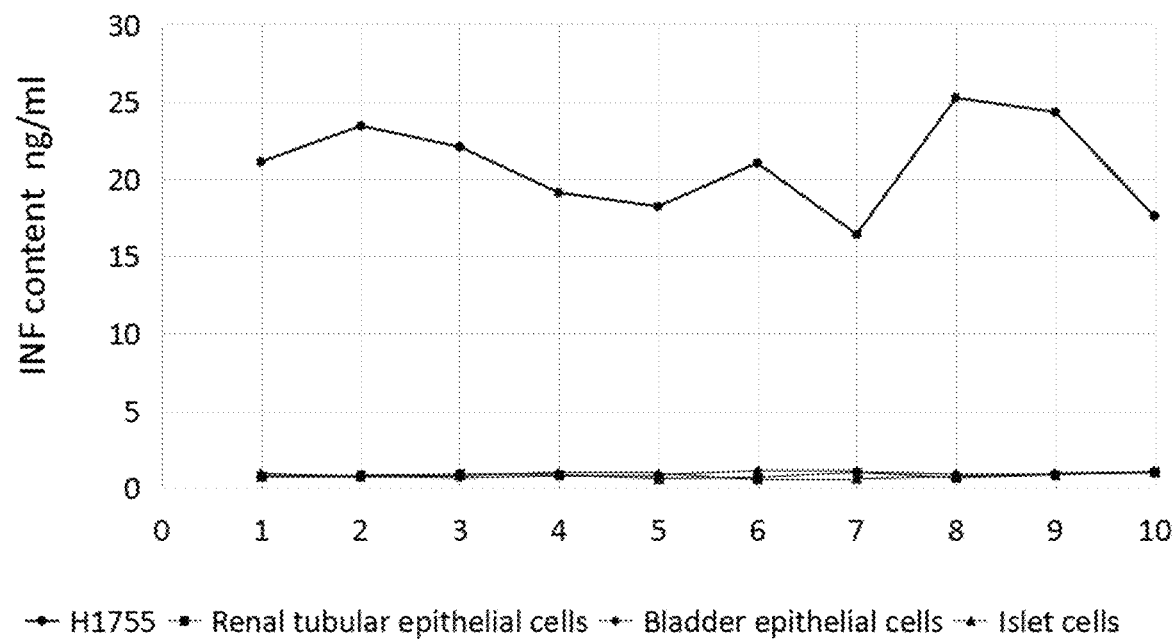

The test results are shown in FIG. 4A-FIG. 4C, in which the abscissa is TCR01-TCR10 and the ordinate is INF content. In FIG. 4A, pulmonary type II alveolar epithelial cells, cardiomyocytes, esophageal epithelial cells and gastric mucosal epithelial cells are illustrated; and in FIG. 4B, small intestinal mucosal epithelial cells, colonic mucosal epithelial cells, gallbladder epithelial cells and hepatic parenchymal cells are illustrated; and in FIG. 4C, renal tubular epithelial cells and bladder epithelial cells are illustrated.

When TCR-T cells according to the present application are injected, INF content in 11 normal tissue cells is maintained at 0-5 ng/ml, approaching 0 ng/ml, indicating that TCR-T cells are basically non-toxic to normal cells, while in positive H1755 (MAGE-A4+, HLA-A02+) tumor cells, the INF content can reach up to 15-255 ng/ml.

Figure 5:
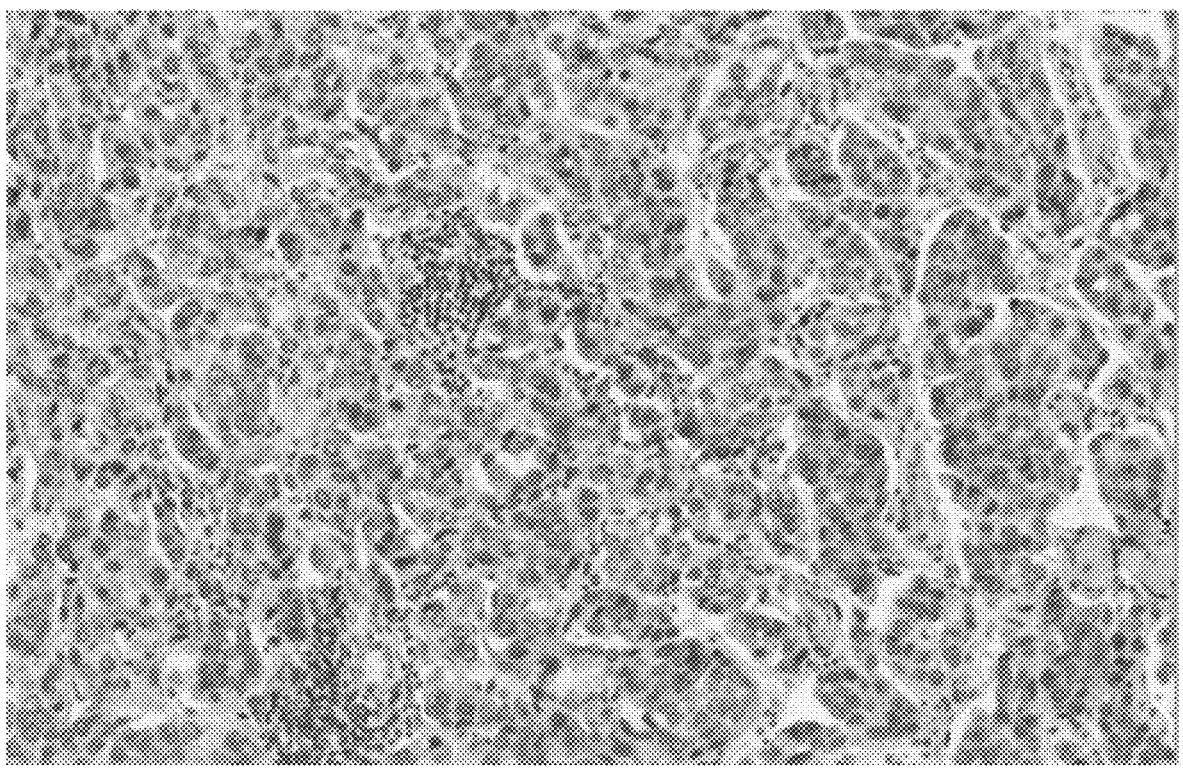
FIG. 5 shows 6PA2021-TCR01 MAGE-A4 IHC pathological staining results (40×) in Example 6.

Example 7 Effect of TCR-T Screened in this Application in Treating Tumor Patients Patient PA2021-TCR01, male, 75 years old, was diagnosed with high-grade papillary urothelial carcinoma of the bladder in September 2020 due to gross hematuria. After performing relevant examinations, bladder space occupation was considered. Transurethral resection of bladder tumor was performed in October 2020. Postoperative pathology showed that high-grade papillary urothelial carcinoma of the bladder infiltrated the muscular layer. PET CT showed positive FDG uptake in multiple pelvic lymph nodes, and metastasis was considered. After diagnosis, the patients were treated with gemcitabine+cisplatin+teplizumab for 4 times. The tumor still progressed after reexamination in March 2021. After being treated with MAGE-A4 TCR-T cells, IHC staining result of tumor pathological white film showed MAGE-A4 positive (FIG. 5), and the HLA typing result of peripheral blood was HLA-A*02:01, as shown in Table 8 below.

TABLE 8

| PA2021-TCR01_HLA | PA2021-TCR01_Read_counts | PA2021-TCR01_HLA_cell_num | PA2021-TCR01_Total_cell_num | PA2021-TCR01_Cell_ratio |
| --- | --- | --- | --- | --- |
| A*02:01:175 | 28510 | 2703 | 2983 | 0.9061 |
| B*08:18 | 31832 | 2671 | 2983 | 0.8954 |
| C*03:47 | 2300 | 1287 | 2983 | 0.4314 |
| C*07:429 | 10576 | 2289 | 2983 | 0.7673 |
| DPA1*01:03:17 | 955 | 531 | 2983 | 0.178 |
| DPA1*02:06 | 20972 | 1499 | 2983 | 0.5025 |
| DPB1*22:01:01:01 | 6010 | 918 | 2983 | 0.3077 |
| DPB1*105:01:01:10 | 6470 | 980 | 2983 | 0.3285 |
| DQA1*03:02:01:02 | 18009 | 1350 | 2983 | 0.4526 |
| DQB1*03:01:01:35 | 10154 | 1177 | 2983 | 0.3946 |
| DRB1*09:01:02:07 | 50977 | 1964 | 2983 | 0.6584 |

Figure 6A:
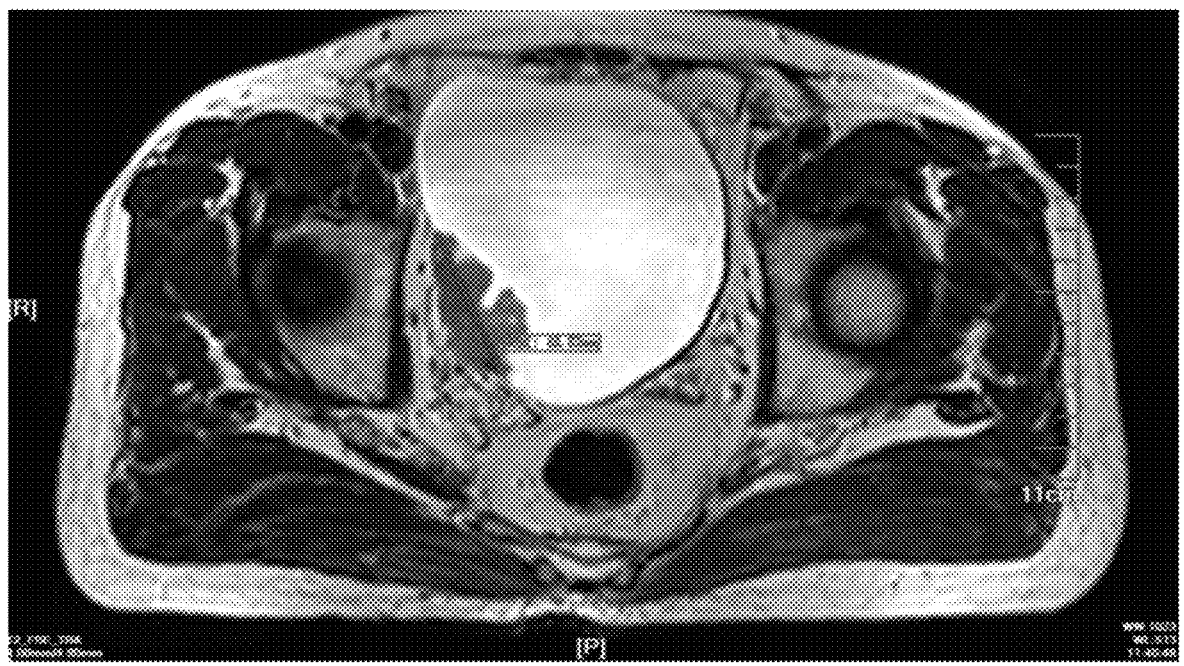
Figure 6B:
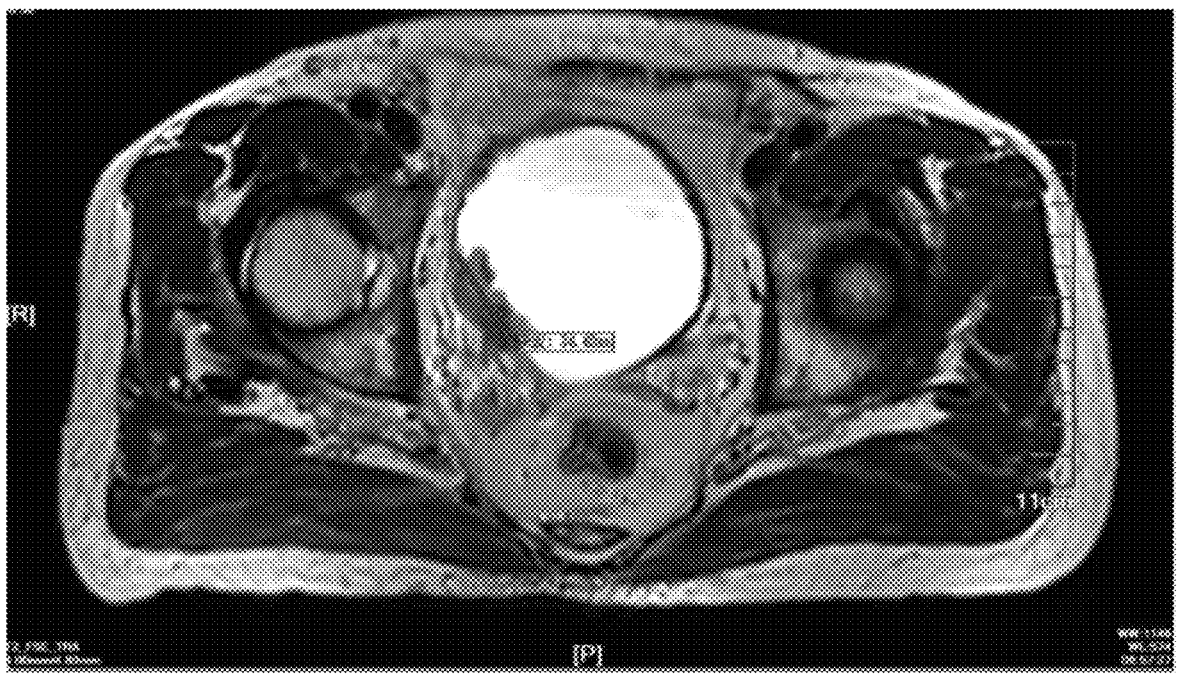

TCR01-05 cell preparation containing 5e$^9$ TCR-T cells were infused intravenously. MR reexamination results on the day of injection (FIG. 6A) and 45 days after injection (FIG. 6B) showed that the focus was reduced and the diffusion was weakened, and the maximum diameter of the tumor was reduced from 48.52 mm to 34.48 mm.

The above examples are only provided for the purpose of explaining the technical concept and characteristics of the application, so as to enable those skilled in the art familiar with the technology and understand the content of the application and implement it. They are not intended to limit the scope of protection of the application. Without departing from the concept, spirit and scope of the application, the method described in the application and the steps or step sequence of the method can be changed. All equivalent changes or modifications made according to the spirit and essence of this application shall be covered by the scope of protection of this application.

What is claimed is:

1. A T cell receptor (TCR), comprising
a TCRα polypeptide comprising CDRα1 having an amino acid sequence comprising SEQ ID No: 64, CDRα2 having an amino acid sequence comprising SEQ ID No:94, and CDRα3 having an amino acid sequence comprising SEQ ID No: 124; and
a TCRβ polypeptide comprising CDRβ1 having an amino acid sequence comprising SEQ ID No: 154, CDRβ2 having an amino acid sequence comprising SEQ ID No: 184, and CDRβ3 having an amino acid sequence comprising SEQ ID No: 214,
wherein the T cell receptor (TCR) further comprises a humanized C domain and/or a murine C domain and/or a modified humanized C domain, wherein the humanized C domain comprises SEQ ID No: 243 or 244, the murine C domain comprises SEQ ID No: 245 or 246, and the modified humanized C domain comprises SEQ ID No: 247 or 248.

2. The T cell receptor (TCR) according to claim 1, wherein the TCRα polypeptide has an amino acid sequence comprising SEQ ID No: 4, and the TCRβ polypeptide has an amino acid sequence comprising SEQ ID No: 34.

3. A cell, comprising a recombinant expression vector containing a polynucleotide encoding a T cell receptor (TCR) operatively cloned therein, wherein the TCR comprises:
a TCRα polypeptide comprising CDRα1 having an amino acid sequence comprising SEQ ID No: 64, CDRα2 having an amino acid sequence comprising SEQ ID No:94, and CDRα3 having an amino acid sequence comprising SEQ ID No: 124; and
a TCRβ polypeptide comprising CDRβ1 having an amino acid sequence comprising SEQ ID No: 154, CDRβ2 having an amino acid sequence comprising SEQ ID No: 184, and CDRβ3 having an amino acid sequence comprising SEQ ID No: 214.

4. The cell according to claim 3, wherein the TCRα polypeptide has an amino acid sequence comprising SEQ ID No: 4, and the TCRβ polypeptide has an amino acid sequence comprising SEQ ID No: 34.

5. The T cell receptor (TCR) according to claim 1, wherein the TCR is capable of specifically recognizing MAGE-A4 antigenic peptide and the MAGE-A4 antigenic peptide is HLA-A2 restricted.

6. The T cell receptor (TCR) according to claim 5, wherein the HLA-A2 is HLA-A*0201 typing.

7. The T cell receptor (TCR) according to claim 1, wherein the T cell receptor (TCR) further comprises a modified linker domain comprising SEQ ID No: 241 or 242.

8. The T cell receptor (TCR) according to claim 1, wherein the humanized C domain or the murine C domain or the modified humanized C domain linked to the TCRα polypeptide and the humanized C domain or the murine C domain or the modified humanized C domain linked to the TCRβ polypeptide are of the same source.

9. The cell according to claim 3, wherein the recombinant expression vector comprises a viral vector.

10. The cell according to claim 9, wherein the viral vector comprises a retroviral vector and a lentiviral vector.

11. The cell according to claim 3, wherein the cell comprises an immune cell.

12. The cell according to claim 3, wherein the cell comprises T cell, NK cell, NKT cell, constant NK cell or other lymphocyte in peripheral blood.

13. The cell according to claim 3, wherein the cell is autologous or allogeneic cell isolated from umbilical cord or blood.

14. A method for treating a tumor in a subject in need thereof, comprising administrating the cell according to claim 3 into the subject, wherein the tumor expresses MAGE-A4, and wherein the cell is an immune cell.

15. The method according to claim 14, wherein the tumor comprises a cancer.

16. The method according to claim 14, wherein the tumor comprises an esophageal cancer, a gastric cancer, a bladder cancer, a head and neck cancer and a sarcoma.

17. The method according to claim 14, wherein the subject is human or a mouse.

* * * * *